US011160599B2

(12) United States Patent
Honda et al.

(10) Patent No.: US 11,160,599 B2
(45) Date of Patent: Nov. 2, 2021

(54) CONTROL DEVICE

(71) Applicant: Olympus Corporation, Hachioji (JP)

(72) Inventors: Yoshitaka Honda, Hachioji (JP); Ojiro Kitamura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 384 days.

(21) Appl. No.: 16/264,801

(22) Filed: Feb. 1, 2019

(65) Prior Publication Data
US 2019/0159822 A1 May 30, 2019

Related U.S. Application Data

(63) Continuation of application No. PCT/JP2016/072973, filed on Aug. 4, 2016.

(51) Int. Cl.
A61B 18/12 (2006.01)
A61B 18/08 (2006.01)
(Continued)

(52) U.S. Cl.
CPC ............ *A61B 18/085* (2013.01); *A61B 18/10* (2013.01); *A61B 17/29* (2013.01);
(Continued)

(58) Field of Classification Search
CPC .................. A61B 18/085; A61B 18/10; A61B 2018/00642; A61B 2018/00672;
(Continued)

(56) References Cited

U.S. PATENT DOCUMENTS 5,277,201 A * 1/1994 Stern ...................... A61B 18/14
606/32
9,119,619 B2 9/2015 Honda et al.
(Continued)

FOREIGN PATENT DOCUMENTS

CN 103997979 A 8/2014
JP 2005-253789 9/2005
(Continued)

OTHER PUBLICATIONS

Dec. 30, 2020 Office Action issued in Chinese Patent Application No. 201680088225.4.
(Continued)

*Primary Examiner* — Daniel W Fowler
(74) *Attorney, Agent, or Firm* — Oliff PLC

(57) ABSTRACT

A control device for use with a treatment tool that includes a heating element to apply heat to a treatment target. The control device comprises a processor configured to set a target temperature for the heating element and to control the heating element so that temperature of the heating element follows the target temperature. The processor is configured to switch the control of the heating element from a first phase to a second phase. A first followability of the temperature of the heating element in the first phase is higher than a second followability of the temperature in the second phase. The processor is configured to terminate the controlling of following the temperature of the heating element to the target temperature when a parameter is beyond a predetermined range wherein the parameter being defined as a fluctuation between the temperature of the heating element and the target temperature.

15 Claims, 11 Drawing Sheets

(51) Int. Cl.
*A61B 18/10* (2006.01)
*A61B 18/00* (2006.01)
*A61B 17/29* (2006.01)
*A61B 17/00* (2006.01)

(52) U.S. Cl.
CPC ........... *A61B 2017/00973* (2013.01); *A61B 2018/0063* (2013.01); *A61B 2018/0072* (2013.01); *A61B 2018/00589* (2013.01); *A61B 2018/00601* (2013.01); *A61B 2018/00642* (2013.01); *A61B 2018/00648* (2013.01); *A61B 2018/00672* (2013.01); *A61B 2018/00678* (2013.01); *A61B 2018/00702* (2013.01); *A61B 2018/00714* (2013.01); *A61B 2018/00767* (2013.01); *A61B 2018/00779* (2013.01); *A61B 2018/00791* (2013.01); *A61B 2018/00827* (2013.01); *A61B 2018/00875* (2013.01); *A61B 2018/00886* (2013.01); *A61B 2018/00892* (2013.01); *A61B 2018/00916* (2013.01)

(58) Field of Classification Search
CPC ........... A61B 2018/00678; A61B 2018/00702; A61B 2018/00886
See application file for complete search history.

(56) References Cited

U.S. PATENT DOCUMENTS

| | | | |
|---|---|---|---|
| 9,155,884 B2 | 10/2015 | Honda et al. | |
| 2002/0082593 A1* | 6/2002 | Hareyama | A61B 18/085 606/38 |
| 2003/0060818 A1 | 3/2003 | Kannenberg et al. | |
| 2005/0222560 A1 | 10/2005 | Kimura et al. | |
| 2009/0259244 A1 | 10/2009 | Shimizu | |
| 2010/0262135 A1* | 10/2010 | Berube | A61B 18/1477 606/33 |
| 2012/0022517 A1 | 1/2012 | Stuebe | |
| 2013/0338665 A1 | 12/2013 | Tanaka et al. | |
| 2014/0031808 A1* | 1/2014 | Phan | A61B 18/1492 606/33 |
| 2014/0148797 A1 | 5/2014 | Yasunaga | |
| 2014/0236140 A1 | 8/2014 | Honda et al. | |

FOREIGN PATENT DOCUMENTS

| | | |
|---|---|---|
| JP | 2005-531367 | 10/2005 |
| JP | 2012-024583 | 2/2012 |
| JP | 2013-034613 | 2/2013 |
| JP | 2014-054546 | 3/2014 |
| WO | 2004002346 | 1/2004 |
| WO | 2013088890 | 6/2013 |
| WO | 2013088893 | 6/2013 |
| WO | 2013187357 | 12/2013 |

OTHER PUBLICATIONS

International Search Report and Written Opinion from corresponding International Application No. PCT/JP2016/072973, dated Nov. 1, 2016.

* cited by examiner

CONTROL DEVICE

CROSS-REFERENCE TO RELATED APPLICATION

This application is a continuation application of PCT Application No. PCT/JP 2016/072973 filed on Aug. 4, 2016, which is hereby incorporated by reference in its entirety.

TECHNICAL FIELD

The disclosed technology relates to a control device for use with an energy treatment tool that applies heat, using a heating element, to a treatment target. The control device controls the temperature of the heating element.

DESCRIPTION OF THE RELATED ART

U. S. Patent Application Publication No. 2012/0022517 discloses a control device that allows a heating element, which is included in an energy treatment tool, to apply heat by transmitting electrical energy to the heating element. With this energy treatment tool, treatment is performed by applying heat the heating element to a treatment target. The control device sets a target resistance value as a target value for a resistance value of the heating element, which varies depending on the temperature of the heating element. With electrical energy being transmitted to the heating element, the control device determines whether or not the resistance value of the heating element falls inside a predetermined range that includes the target resistance value. If the resistance value falls outside the predetermined range, the control device terminates the output of the electrical energy to the heating element.

If a treatment target is cut using such an energy treatment tool and control device as disclosed in U.S. Patent Application Publication No. 2012/0022517, it is desired from the viewpoint of treatment performance that, until the treatment target is cut to a desired extent with heat generated at a heating element, the resistance value of the heating element is maintained at a target resistance value over time and the temperature of the heating element is maintained at a target temperature over time. For this purpose, the control device sets a control parameter so that the followability of the temperature of the heating element to the target temperature becomes higher, and controls the supply of electrical energy to the heating element and the temperature of the heating element.

BRIEF SUMMARY OF EMBODIMENTS

One aspect of the disclosed technology is directed to a control device for use with a treatment tool that includes a heating element to apply heat to a treatment target. The control device comprises a processor configured to set a target temperature for the heating element and to control the heating element so that temperature of the heating element follows the target temperature. The processor is configured to switch, based on satisfaction of a predetermined condition, the control of the heating element from a first phase to a second phase. A first followability of the temperature of the heating element in the first phase is higher than a second followability of the temperature in the second phase. The processor is configured to terminate the controlling of following the temperature of the heating element to the target temperature when a parameter is beyond a predetermined range wherein the parameter being defined as a fluctuation between the temperature of the heating element and the target temperature.

Another aspect of the disclosed technology is directed to a control device for use with a treatment tool that includes a heating element. The control device comprises an energy output source configured to transmit electrical energy to the heating element so as to apply heat to a treatment target. A processor is configured to be in electrical communication with the energy output source so as to control temperature of the heating element by controlling the output of the electrical energy from the energy output source. The processor is configured to set a target temperature for the heating element and to control the output of the electrical energy so that the temperature of the heating element follows the target temperature. Based on an output state of the electrical energy from the energy output source to the heating element, to set a target trend for an electrical characteristic value relating to the electrical energy, the target trend representing variations in the electrical characteristic value over time if the temperature of the heating element is maintained at the target temperature over time after the temperature of the heating element has reached the target temperature. Based on satisfaction of a predetermined condition, to switch the control of the electrical energy, which is to be transmitted to the heating element from a first phase to a second phase wherein a first followability of the temperature of the heating element in the first phase is higher than a second followability of the temperature in the second phase, and to reduce the output of the electrical energy from the energy output source to the heating element so that the temperature of the heating element decreases to a temperature, at which no substantial tissue degeneration occurs in the treatment target, when a parameter is beyond a predetermined range wherein the parameter being defined as a fluctuation between the electrical characteristic value and the target trend. The processor uses, as the electrical characteristic value, one of output power, output current and output voltage from the energy output source to the heating element.

A Further aspect of the disclosed technology is directed to a treatment system comprises an energy treatment tool. A control device is configured to be attached to the energy treatment tool so as to enable the treatment system to conduct a treatment on a body tissue. The control device comprises an energy output source configured to transmit electrical energy to a heating element so as to apply heat to a treatment target. A processor is configured to be in electrical communication with the energy output source so as to control temperature of the heating element by controlling the output of the electrical energy from the energy output source. The processor is configured by setting a target temperature for the heating element and controlling the output of the electrical energy so that the temperature of the heating element follows the target temperature. Next, setting a target trend for an electrical characteristic value relating to the electrical energy, the target trend representing variations in the electrical characteristic value over time if the temperature of the heating element is maintained at the target temperature over time after the temperature of the heating element has reached the target temperature. Next, switching the control of the electrical energy, which is to be transmitted to the heating element from a first phase to a second phase wherein a first followability of the temperature of the heating element in the first phase is higher than a second followability of the temperature in the second phase. Finally, reducing the output of the electrical energy from the energy output source to the heating element so that the temperature of the heating element decreases to a temperature, at which no substantial tissue degeneration occurs in the treatment target, when a parameter is beyond a predetermined range wherein the parameter being defined as a fluctuation between the electrical characteristic value and the target trend.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

FIRST EMBODIMENT

With reference to FIGS. 1 through 10, a description will be made about a first embodiment of the disclosed technology.

Figure 1:
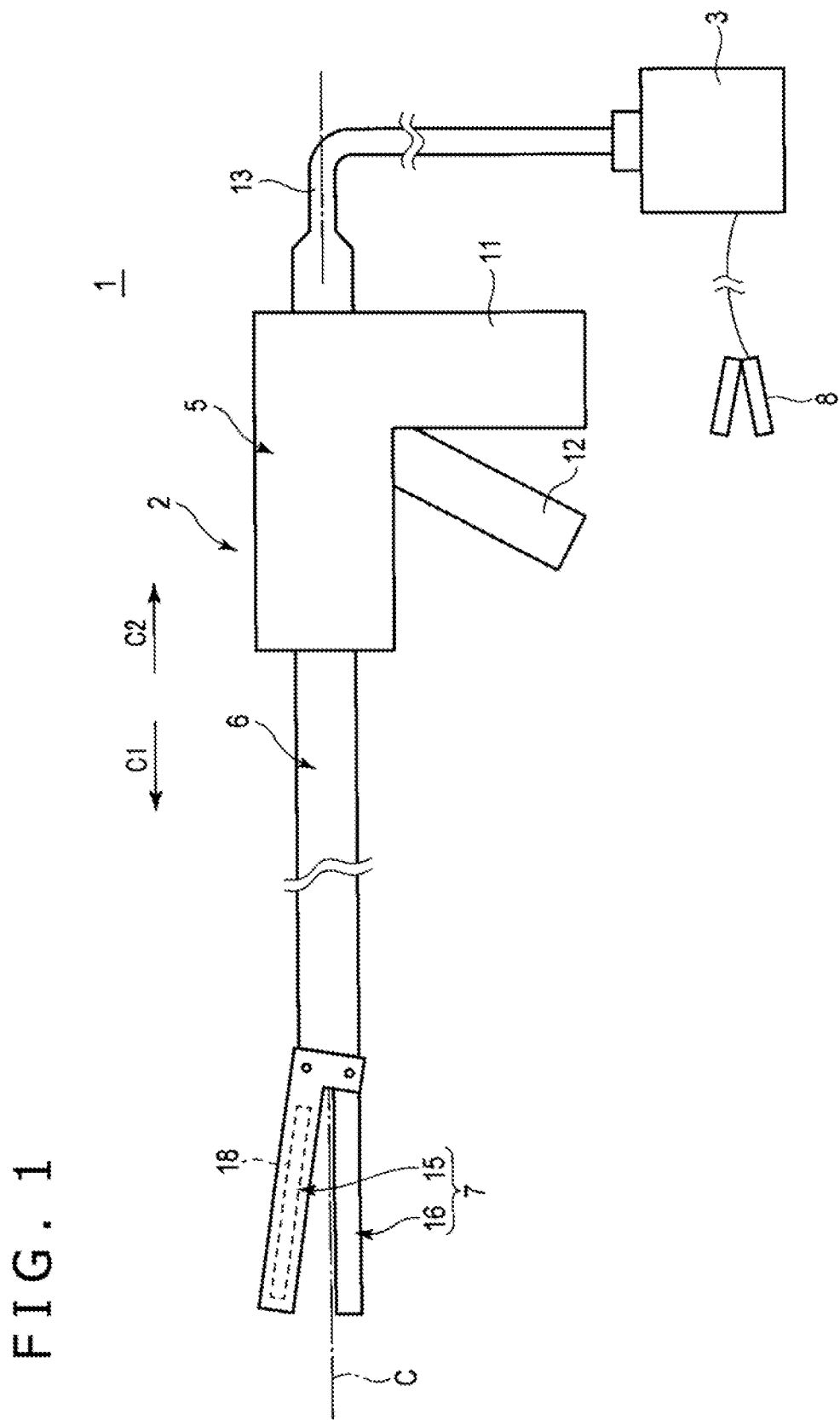
FIG. 1 is a schematic view depicting a treatment system according to a first embodiment.

FIG. 1 is a view depicting a treatment system 1 of this embodiment. As depicted in FIG. 1, the treatment system 1 includes an energy treatment tool 2 and a control device 3. The energy treatment tool 2 has a longitudinal axis C. Here, one of directions along the longitudinal axis C is defined to be "a distal end side" or "a side indicated by arrow C1," while a side opposite to the distal side is defined to be "a proximal end side" or "a side indicated by arrow C2."

The energy treatment tool 2 includes a holdable housing 5, a shaft or sheath 6 connected to a distal end side of the housing 5, and an end effector 7 disposed on a distal end portion of the shaft 6. The shaft 6 has a central axis, which is substantially coaxial with the longitudinal axis C. On the housing 5, a grip 11 is disposed, and further a handle 12 is pivotally secured. Through pivotal movement of the handle 12 relative to the housing 5, the handle 12 opens or closes relative to the grip 11.

The end effector 7 includes a first grasping jaw 15 and a second grasping jaw 16. By opening or closing the handle 12 relative to the grip 11, the paired grasping jaws 15 and 16 open from each other or close together. By closing the paired grasping jaws 15 and 16 together, a treatment target such as biological tissue can be grasped between the grasping jaws 15 and 16. In an example, one of the grasping jaws 15 and 16 is formed integrally with the shaft 6, or is fixed on the shaft 6. The other one of the grasping jaws 15 and 16 is pivotally secured on the shaft 6. In another example, the grasping jaws 15 and 16 are both pivotally secured on the shaft 6.

In the end effector 7, a heating element 18 such as a heater is disposed. The heating element 18 may be disposed in only one of the grasping jaws 15 and 16, or heating elements 18 may be disposed in the grasping jaws 15 and 16, respectively. In the embodiment of FIG. 1, the heating element 18 is disposed in only the first grasping jaw 15. By supplying electrical energy to the heating element 18, heat is generated at the heating element 18. The heat generated at the heating element 18 is then applied as treatment energy to the treatment target grasped between the grasping jaws 15 and 16.

A cable 13 is connected at an end thereof to the housing 5. The cable 13 is connected at an opposite end thereof separably to the control device 3. The treatment system 1 also includes a footswitch 8 as an energy operation input portion. The footswitch 8 is electrically connected to the control device 3. Through the footswitch 8, an operation is inputted to transmit electrical energy from the control device 3 to the heating element 18 of the energy treatment tool 2. Instead of or in addition to the footswitch 8, an operation button or the like which is secured on the housing 5 of the energy treatment tool 2 may be disposed as an energy operation input portion.

Figure 2:
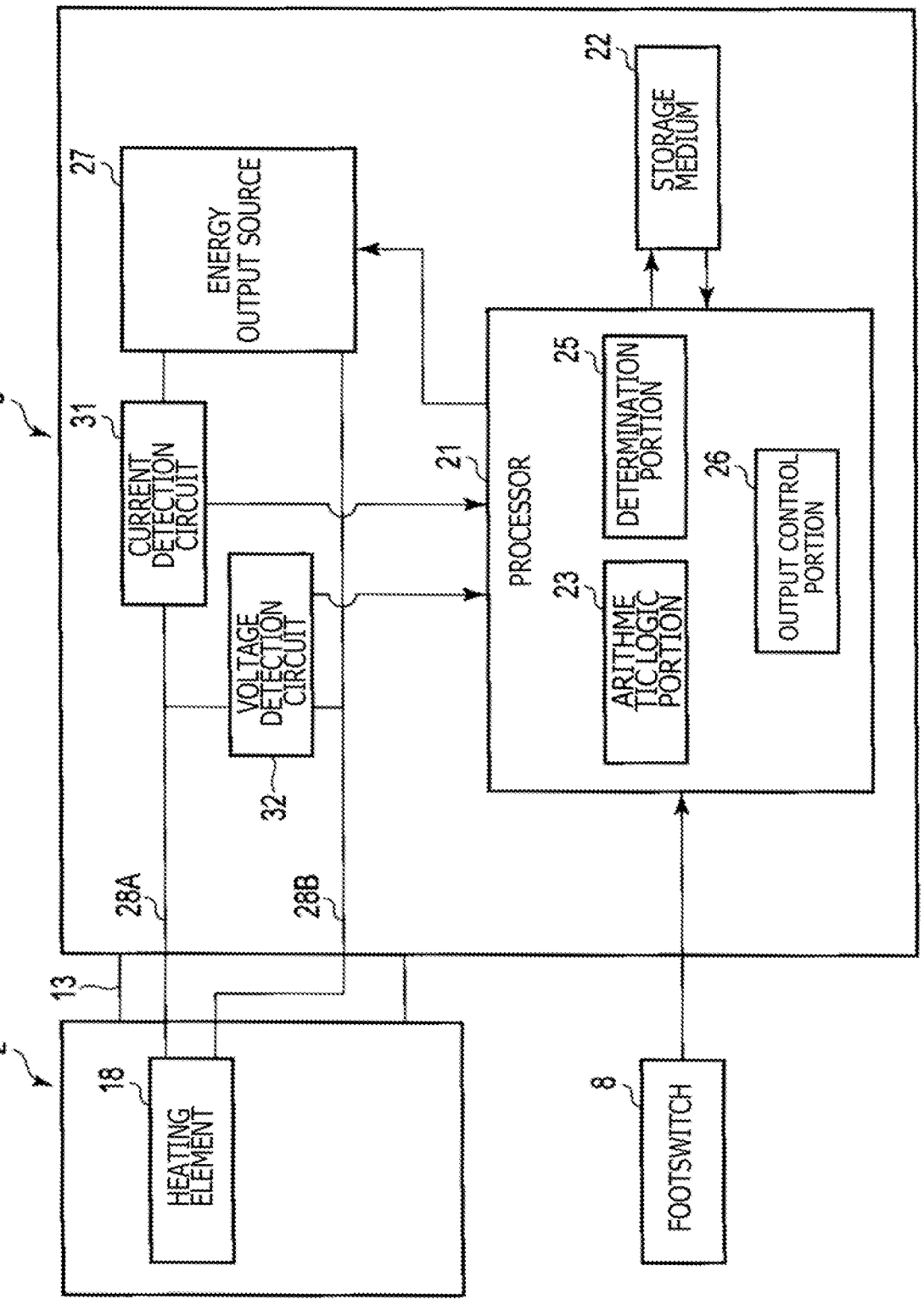
FIG. 2 is a block diagram representing a configuration relating to the supply of electrical energy from a control device to an energy treatment tool in the first embodiment.

FIG. 2 is a diagram representing a configuration relating to the supply of electrical energy from the control device 3 to the energy treatment tool 2. As represented in FIG. 2, the control device 3 includes a processor 21, which controls the whole treatment system 1, and a storage medium 22. The processor or control portion 21 is formed from an integrated circuit that includes a central processing unit (CPU), an application specific integrated circuit (ASIC), a field programmable gate array (FPGA), or the like. The processor 21 may be formed from a single integrated circuit, or may be formed from a plurality of integrated circuits. In the control device 3, on the other hand, the processor 21 may be disposed as a single unitary processor, or the processor 21 may be disposed as a plurality of discrete processors. Processing at the processor 21 is performed in accordance with programs stored in the processor 21 or storage medium 22. Stored in the storage medium 22 are the processing programs to be used at the processor 21, parameters, tables and the like to be used in arithmetic logic operations at the processor 21. The processor 21 includes an arithmetic logic portion 23, a determination portion 25 and an output control portion 26. The arithmetic logic portion 23, determination portion 25 and output control portion 26 function as parts of the processor 21, and perform parts of the processing to be performed by the processor 21.

The control device 3 includes an energy output source 27. The energy output source 27 is electrically connected to the heating element 18 via electrical pathways 28A and 28B disposed extending internally through the cable 13 and housing 5. The energy output source 27 includes a conversion circuit or the like that converts electrical power, which is supplied from a battery power supply or a receptacle power source, to electrical energy to be supplied to the heating element 18. If an operation is inputted through the footswitch 8, the processor 21 causes the energy output source 27 to output the electrical energy which has been converted through the conversion circuit. The electrical energy outputted from the energy output source 27 is then supplied to the heating element 18 via the electrical pathways 28A and 28B. The output control portion 26 of the processor 21 controls the output of electrical energy from the energy output source 27. From the energy output source 27, direct-current power or alternating-current power is outputted as electrical energy.

The treatment system 1 includes a current detection circuit 31 and a voltage detection circuit 32. The current detection circuit 31 detects an output current I from the energy output source 27 to the heating element 18, and the voltage detection circuit 32 detects an output voltage V from the energy output source 27 to the heating element 18. The detection result of the output current I at the current detection circuit 31 and the detection result of the output voltage V at the voltage detection circuit 32 are transmitted to the processor 21. The arithmetic logic portion 23 of the processor 21 calculates a resistance value R of the heating element 18 based on the detected output current I and output voltage V. The current detection circuit 31 and voltage detection circuit 32 may be disposed in the control device 3 or in the energy treatment tool 2.

A description will next be made about functions and effects of the control device 3 and treatment system 1. Upon treatment of a treatment target with the treatment system 1, a surgeon holds the housing 5, and inserts the end effector 7 into a body cavity such as an abdominal cavity. The treatment target such as a blood vessel is then placed between the grasping jaws 15 and 16, and the handle 12 is closed relative to the grip 11. As a consequence, the treatment target is grasped between the grasping jaws 15 and 16. In this state, the surgeon performs an operation input through the footswitch 8. As a consequence, electrical energy is transmitted from the energy output source 27 to the heating element 18, and heat is generated at the heating element 18. The heat generated at the heating element 18 is applied to the grasped treatment target so that the treatment target is coagulated, sealed or cut.

Figure 3:
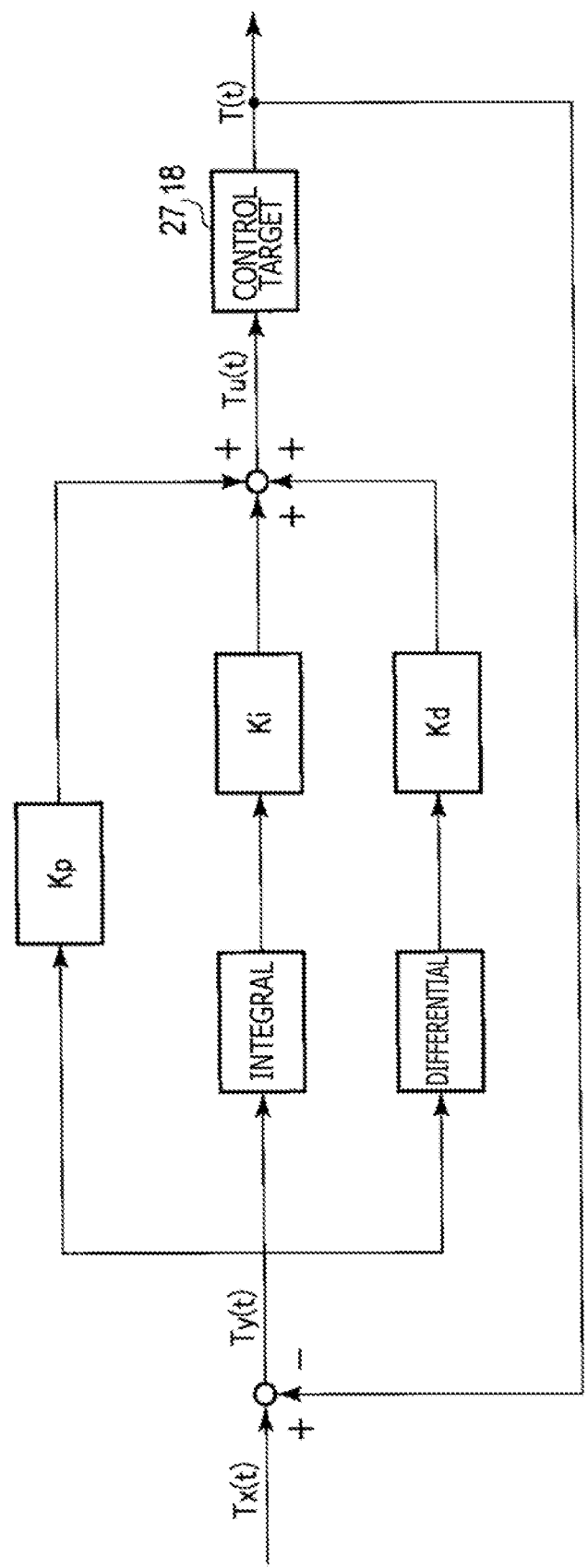
FIG. 3 is a block diagram illustrating proportional-integral-differential (PID) control by a processor in the first embodiment.

In the state that the electrical energy is supplied from the energy output source 27 to the heating element 18 and the heat is generated at the heating element 18, the processor 21 controls control targets, which include the energy output source 27 and heating element 18, by PID control that is a kind of feedback control. FIG. 3 is a diagram illustrating PID control by the processor 21. Here, time t is defined as a variable.

As illustrated in FIG. 3, the processor 21 controls the temperature $T(t)$ of the heating element 18, in other words, an output from the control target as a control variable in this embodiment. The resistance value R of the heating element 18 varies depending on the temperature T of the heating element 18. In other words, the resistance value R increases with the temperature T, and the resistance value R decreases with the temperature T. As mentioned hereinbefore, the resistance value R is calculated based on the output current I and output voltage V. In this embodiment, a table, function or the like, which represents a correlation between temperatures T and resistance values R, is stored in the storage medium 22. The arithmetic logic portion 23 of the processor 21 determines the temperature $T(t)$, which is a control variable, based on the correlation between resistance values R and temperatures T.

In PID control of the temperature $T(t)$ of the heating element 18, the processor 21 sets a target temperature $Tx(t)$ for the heating element 18 at a time t. The arithmetic logic portion 23 of the processor 21 then calculates a temperature difference $Ty(t)$ by subtracting the temperature $T(t)$ from the target temperature $Tx(t)$. The processor 21 then sets an operation variable $Tu(t)$ as an input to the control target based on the temperature difference $Ty(t)$.

In the setting of the operation variable Tu(t), the processor 21 multiplies the temperature difference Ty(t) by a proportional gain Kp to calculate the term of proportional action in the operation variable Tu(t). Further, the processor 21 performs time integration of the temperature difference Ty(t) to calculate an integrated value Σ(t)Ty of the temperature difference Ty(t) from the time of beginning of an output of electrical energy from the energy output source 27 or a moment determined under a predetermined condition until the time t. The arithmetic logic portion 23 of the processor 21 then multiplies the integrated value Σ(t)Ty by an integral gain Ki to calculate the term of integral action in the operation variable Tu(t). Furthermore, the processor 21 performs time derivation of the temperature difference Ty(t) to calculate a time change rate ΔTy(t) of the temperature difference Ty(t) at the time t. The arithmetic logic portion 23 of the processor 21 then multiplies the time change rate ΔTy(t) by a derivative gain Kd to calculate the term of derivative action in the operation variable Tu(t). Moreover, the processor 21 performs addition of the calculated term of proportional action, the calculated term of integral action and the calculated term of derivative action to determine the operation variable Tu(t) for the control target in the PID control. Therefore, the operation variable Tu(t) can be expressed as formula (1). The proportional gain Kp, integral gain Ki and derivative gain Kd are used as control parameters in the PID control.

$$Tu(t)=Kp \cdot Ty(t)+Ki \cdot E(t)Ty+Kd \cdot \Delta Ty(t) \quad (1)$$

A change in the operation variable Tu(t) leads to a variation in power W to be outputted from the energy output source 27 to the heating element 18, and further to a variation in the quantity of heat to be generated at the heating element 18. As a consequence, the temperature T(t), as a control variable, of the heating element 18 is adjusted. In other words, the processor 21 adjusts the operation variable Tu(t), whereby the output of electrical energy to the heating element 18 is controlled and the temperature T(t) of the heating element 18 is hence controlled. Here, the operation variable Tu(t) is set at zero while the temperature T(t) remains constant at the target temperature Tx(t) over time. If the operation variable Tu(t) is positive, the processor 21 increases the output power W from the energy output source 27 to the heating element 18 to make greater the quantity of heat to be generated at the heating element 18, compared with the case that the temperature T(t) remains constant at the target temperature Tx(t) over time. Here, both the output current I and output voltage V from the energy output source 27 to the heating element 18 also increase compared with the case that the temperature T(t) remains constant at the target temperature Tx(t) over time. If the operation variable Tu(t) is negative, on the other hand, the processor 21 decreases the output power W from the energy output source 27 to the heating element 18 to make smaller the quantity of heat to be generated at the heating element 18, compared with the case that the temperature T(t) remains constant at the target temperature Tx(t) over time. Here, both the output current I and output voltage V from the energy output source 27 to the heating element 18 also decrease compared with the case that the temperature T(t) remains constant at the target temperature Tx(t) over time. By the determination of the operation variable Tu(t) as mentioned hereinbefore, the processor 21 performs feedback control of the temperature T(t) so that the temperature T(t) follows the target temperature Tx(t). The output power W, output current I and output voltage V are electrical characteristic values relating to electrical energy to be transmitted from the energy output source 27 to the heating element 18.

In PID control, the effect of proportional action increases with proportional gain Kp. Similarly, the effect of integral action increases with integral gain Ki, and the effect of derivative action increases with derivative gain Kd. By individually changing the proportional gain Kp, integral gain Ki and derivative gain Kd as control parameters, the followability of temperature T(t) to a target temperature Tx(t) varies in PID control. If the derivative gain Kd is increased to make greater the effect of derivative action, for example, the followability of the temperature T(t) to the target temperature Tx(t) is heightened.

In an example, an integral time τi may be used as a control parameter instead of the integral gain Ki, and a derivative time τd may also be used as a control parameter instead of the derivative gain Kd. Here, the integral gain Ki is a value obtained by dividing the proportional gain Kp with the integral time τi. The integral time τi, on the other hand, represents a time until the term of proportional action and the term of integral action have the same magnitude in the operation variable Tu(t) if an offset of the temperature T(t) by a constant magnitude from the target temperature Tx(t) has continued, in other words, if the temperature difference Ty(t) has remained constant over time. In PID control, the effect of integral action increases as the integral time τi becomes shorter. The derivative gain Kd is a value obtained by multiplying the proportional gain Kp with the derivative time τd. The derivative time τd, in turn, represents a time until the term of proportional action and the term of derivative action have the same magnitude in the operation variable Tu(t) if variations in the temperature T(t) at a constant change rate have continued, in other words, if the time change rate ΔTy(t) of the temperature difference Ty(t) has remained constant over time. In PID control, the effect of derivative action increases as the derivative time τd becomes longer.

In a modification, a resistance value R(t) of the heating element 18 may be used instead of the temperature T(t) as a control variable. In this case, a target resistance value Rx(t) for the heating element 18 is used instead of its target temperature Tx(t), and a resistance value difference Ry(t) is calculated like the temperature difference Ty(t). Like the operation variable Tu(t), the operation variable Ru(t) as an input to the control target is calculated based on the resistance value difference Ry(t). The target resistance value Rx(t) corresponds to the resistance value R when the temperature (T) has reached the target temperature Tx(t). If the resistance value R(t) is used as a control variable, the processor 21 controls the resistance value R(t) so as to follow the target resistance value Rx(t). Here, the resistance value R varies depending on the temperature T. By also controlling the temperature T(t) so as to follow the target temperature Tx(t), the resistance value R(t) is, therefore, also controlled so as to follow the target resistance value Rx(t).

Figure 4:
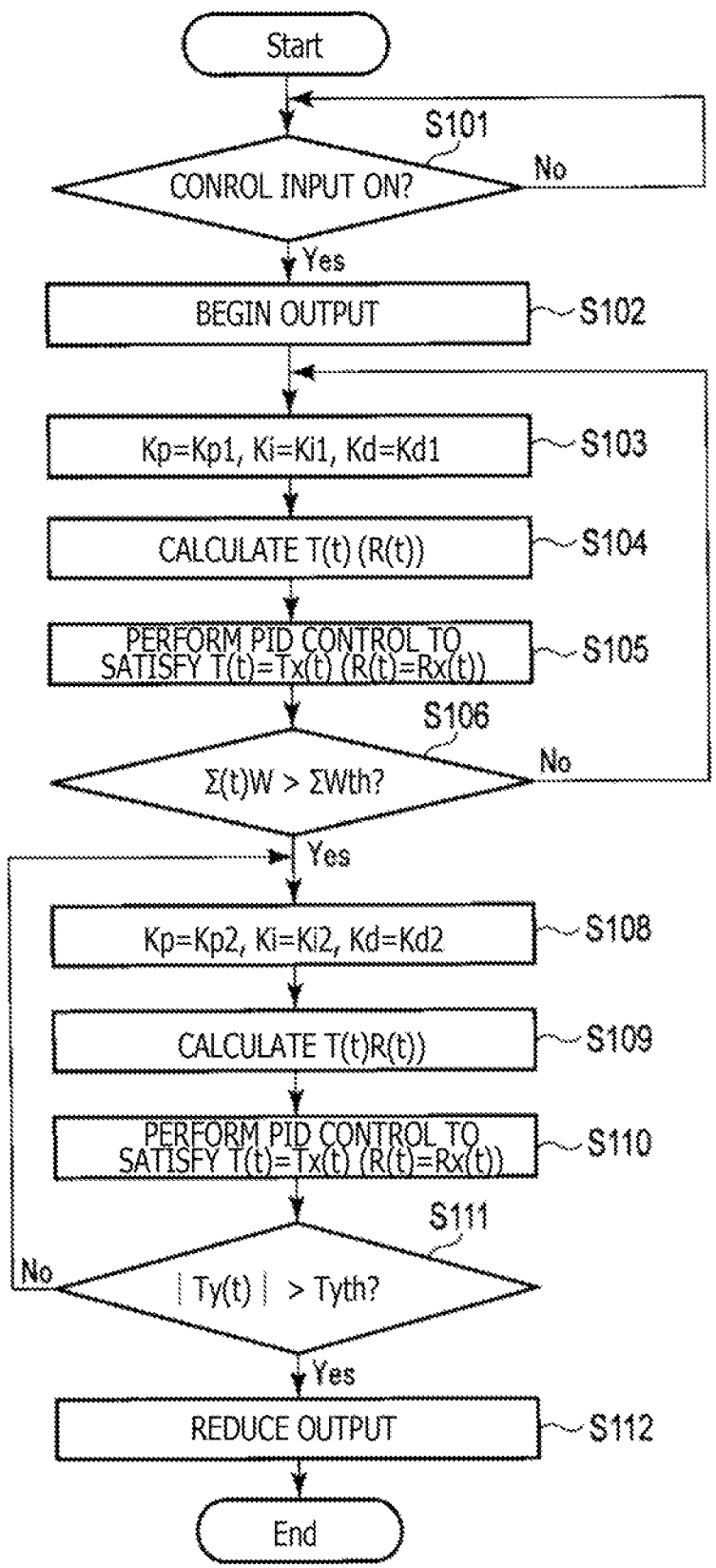
FIG. 4 is a flow chart representing processing at the processor in the first embodiment.

FIG. 4 is a flow chart representing the processing at the processor 21. As represented in FIG. 4, in the processing, the processor 21 determines in Step S101 whether or not an operation input has been performed through the footswitch 8. If no operation input has been performed or if No in Step 101, the processing returns to Step S101. In other words, the processor 21 waits until an operation input is performed through the footswitch 8. If an operation input is determined to have been performed or if Yes in Step S101, the output control portion 26 of the processor 21 causes to begin outputting electrical energy from the energy output source 27 to the heating element 18 in Step S102.

If the output of electrical energy has been begun, the processor 21 sets a target temperature Tx(t). The output control portion 26 of the processor 21 then sets the proportional gain Kp at a set value Kp1, the integral gain Ki at a set value Ki 1, and the proportional gain Kd at a set value Kd1 in Step S103. In Step S104, the arithmetic logic portion 23 of the processor 21 then calculates the resistance value R(t) of the heating element 18 from an output current I and an output voltage V, and calculates the temperature T(t) of the heating element 18 as mentioned hereinbefore. In Step S105, using the set values Kp1, Ki1, and Kd1 as first set values, the output control portion 26 of the processor 21 then performs PID control so that the temperature T(t) follows the target temperature Tx(t). In this step, the output control portion 26 of the processor 21 may perform PID control so that the resistance value R(t) follows a target resistance value Rx(t). Here, the state that the processor 21 performs PID control of the temperature T(t) or the resistance value R(t) of the heating element 18 by the control parameters Kp, Ki, and Kd set at the set values Kp1, Ki1, and Kd1 is defined to be a first phase. In the first phase, the control parameters Kp, Ki, and Kd are set at the set values Kp1, Ki1, and Kd1 at which the followability of the temperature T(t) to the target temperature Tx(t) is heightened. In another example, the set value Kd1 for the derivative gain Kd is increased to make greater the effect of derivative action, whereby the followability of the temperature T(t) to the target temperature Tx(t) is heightened.

In step S106, the determination portion 25 of the processor 21 then calculates the integrated value Σ(t)W of the output power W, for example, from the time of beginning of the output to the time (t), and determines whether or not the integrated value Σ(t)W is greater than a predetermined threshold ΣWth. Here, the predetermined threshold ΣWth may be stored in the storage medium 22, or may be inputted through an input portion (not depicted), such as a touch panel, disposed at the control device 3. As an alternative, the predetermined threshold ΣWth may be fixed at a predetermined value, or may be set based on variations or the like in the output power W over time. Based on whether or not a predetermined condition has been satisfied, the determination portion 25 determines whether or not a treatment target has been cut to a desired extent with heat generated at the heating element 18. In this embodiment, the determination portion 25 of the processor 21 determines, based on whether or not the integrated value Σ(t)W of the output power W is greater than the predetermined threshold ΣWth, whether or not the treatment target has been cut to a desired extent with heat of the heating element 18. If the integrated value Σ(t)W is greater than the predetermined threshold ΣWth or if Yes in Step S106, the processing proceeds to Step S108.

If the integrated value Σ(t)W is equal to or smaller than the predetermined threshold ΣWth or if No in Step S106, the processing returns to Step 103. The processing in Step S103 onwards is then performed sequentially. In this embodiment, the first phase is, therefore, maintained from the time of beginning of the output of electrical energy to the heating element 18 insofar as the integrated value Σ(t)W is equal to or smaller than the predetermined threshold ΣWth.

In Step S108, the processor 21 then sets the proportional gain Kp at a set value Kp2, the integral gain Ki at a set value Ki2, and the derivative gain Kd at a set value Kd2. In other words, if the integrated value Σ(t)W has become greater than the predetermined threshold ΣWth and the predetermined condition has been satisfied in Step 106 or if Yes in Step S106, the processor 21 changes the control parameters Kp, Ki, and Kd from the set values or first set values Kp1, Ki1, and Kd1 to other set values Kp2, Ki2, and Kd2 as second set values in step S108. In Step S109, the processor 21 then calculates the resistance value R(t) of the heating element 18 from the output current value I and output voltage value V, and calculates the temperature T(t) of the heating element 18 as mentioned hereinbefore. In Step S110, using the changed set values or second set values Kp2, Ki2, and Kd2, the output control portion 26 of the processor 21 then performs PID control so that the temperature T(t) follows the target temperature Tx(t). In this step, the output control portion 26 of the processor 21 may perform PID control so that the resistance value R(t) follows the target resistance value Rx(t).

Here, the state that the processor 21 performs PID control of the temperature T(t) or resistance value R(t) of the heating element 18 by the control parameters Kp, Ki, and Kd set at the set values Kp2, Ki2, and Kd2 is defined to be a second phase. In this embodiment, based on the determination that the predetermined condition has been satisfied and the treatment target has been cut to a desired extent with heat of the heating element 18, the processor 21 changes the control parameters Kp, Ki, and Kd as mentioned hereinbefore to switch the control to the heating element 18 from the first phase to the second phase. In the second phase, the control parameters Kp, Ki, and Kd are set at the set values Kp2, Ki2, and Kd2 at which the followability of the temperature T(t) to the target temperature Tx(t) becomes lower than that in the first phase. In a further example, the set value or second set value Kd2 of the derivative gain Kd in the second phase is set smaller than the set value or first set value Kd1 in the first phase. As a consequence, the effect of derivative action is reduced in the second phase than in the first phase so that the followability of the temperature T(t) to the target temperature Tx(t) is lowered. If the derivative time τd is used as a control parameter instead of the derivative gain Kd, the set value τd2 for the derivative time τd in the second phase may be set shorter than the set value τd1 in the first phase. As a consequence, the effect of derivative action becomes smaller, and the followability of the temperature T(t) to the target temperature Tx(t) is lowered in the second phase than in the first phase.

In Step S111, the processor 21 then determines whether or not the absolute value of the temperature difference Ty(t) is greater than a predetermined threshold Tyth. In other words, a determination is made as to whether or not the temperature difference Ty(t) at the time t has fallen outside a predetermine range of a minimum value −Tyth as a negative threshold, or greater but a maximum value Tyth as a positive threshold, or smaller. The predetermined threshold Tyth is set like the predetermined threshold ΣWth. If the absolute value of the temperature difference Ty(t) is greater than the predetermined threshold Tyth, in other words, if the temperature difference Ty(t) has fallen outside the predetermined range or if Yes in Step S111, the processing proceeds to Step S112. If the absolute value of the temperature difference Ty(t) is equal to or smaller than the predetermined threshold Tyth, in other words, if the temperature difference Ty(t) has fallen inside the predetermined range or if No in Step S111, the processing returns to Step S108. Then, the processing in Step S108 onwards is performed sequentially. In this embodiment, after the integrated value Σ(t)W has become greater than the predetermined threshold ΣWth and the predetermined condition has been satisfied, the second phase is, therefore, maintained insofar the absolute value of the temperature difference Ty(t) is equal to or smaller than the predetermined threshold Tyth.

In step S112, the processor 21 reduces the output of electrical energy from the energy output source 27 to the heating element 18 so that the temperature of the heating element 18 decreases to a temperature at which no substantial tissue degeneration occurs in the treatment target. This reduction in the output also includes termination of the output of electrical energy (this will apply equally hereinafter). In this embodiment, based on the falling of the temperature difference Ty(t) outside the predetermined range, the output of electrical energy to the heating element 18 is, therefore, reduced in the second phase to terminate the control that would otherwise allow the temperature T of the heating element 18 to follow the target temperature Tx. The temperature difference Ty(t) is a parameter that represents a fluctuation in the temperature T(t) of the heating element 18 from the target temperature Tx(t).

Figure 5:
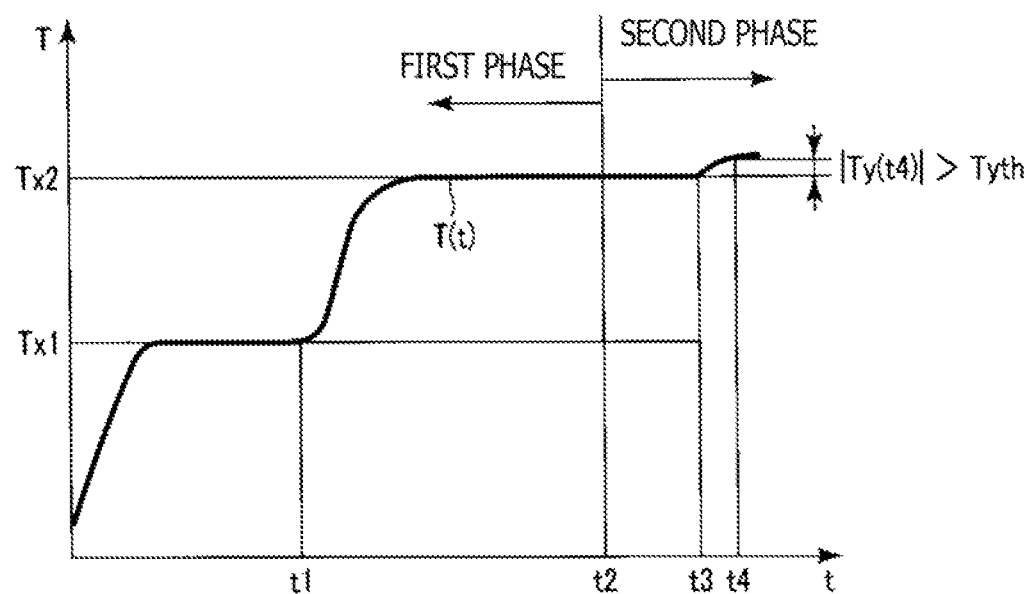
FIG. 5 is a graphic representation of an example of variations in the temperature of a heating element over time if the control is performed by the processor in the first embodiment.
Figure 6:
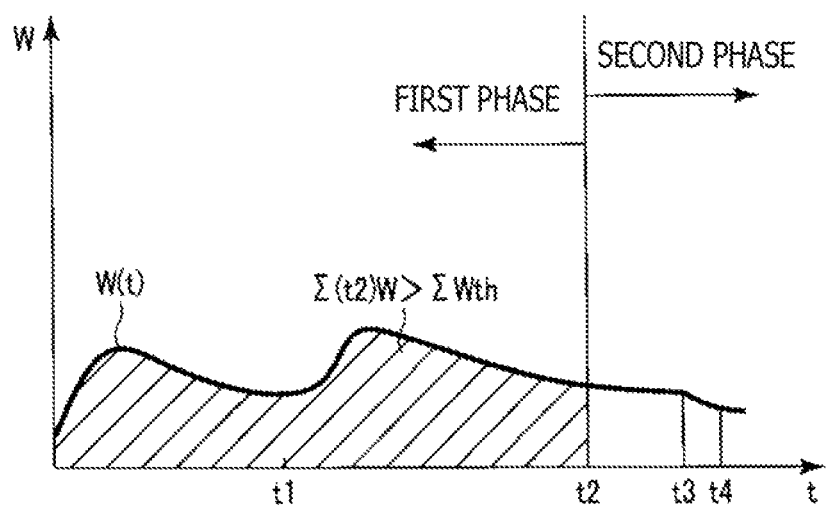
FIG. 6 is a graphic representation of variations in the output power to the heating element over time if the temperature of the heating element has varied as in FIG. 5 in the control by the processor in the first embodiment.

FIG. 5 represents an example of variations in the temperature T of the heating element 18 over time if control is performed by the processor 21, and FIG. 6 represents variations in the output power W to the heating element 18 over time if the temperature T has varied as in FIG. 5. In FIGS. 5 and 6, time t is plotted along a horizontal axis. In FIG. 5, temperature T is plotted along a vertical axis, and in FIG. 6, output power W is plotted along a vertical axis. In the example of FIGS. 5 and 6, the target temperature Tx(t) is set at a temperature Tx1 until a time t1, and after the time t1, is set at a temperature Tx2 which is higher than the temperature Tx1. In the state that the temperature T(t) is allowed to follow the target temperature Tx1, the grasped treatment target is coagulated or sealed with heat of the heating element 18. In the state that the temperature T(t) is allowed to follow the target temperature Tx2, the treatment target is cut with heat of the heating element 18.

Here, until the treatment target is cut to a desired extent from the beginning of the output, in other words, until the integrated value $\Sigma(t)W$ of the output power W becomes greater than the predetermined threshold $\Sigma Wth$ and the predetermined condition is satisfied, the first phase mentioned hereinbefore is maintained so that the followability of the temperature T(t) to the target temperature Tx(t) is heightened. In other words, the control parameters Kp, Ki, and Kd are set at the set value or first set values Kp1, Ki1, and Kd1 at which the followability of the temperature T(t) to the target temperature Tx(t) is heightened. Before the time t1, the temperature T(t), therefore, rises to the target temperature Tx1 rapidly from the beginning of the output. After risen to the target temperature Tx1, the temperature T(t) remains at the target temperature Tx1 without substantial fluctuations. Similarly, at and after the time t1, the temperature T(t) rapidly rises to the target temperature Tx2. After risen to the target temperature Tx2, the temperature T(t) remains at the target temperature Tx2 without substantial fluctuations. Therefore, in the first phase in which the treatment target is cut to a desired extent, heat of the heating element 18 is appropriately applied to the treatment target so that the treatment target is appropriately coagulated and sealed, and is also appropriately cut to a desired extent. Accordingly, appropriate treatment performance is ensured for the treatment target.

In the example of FIGS. 5 and 6, the integrated value $\Sigma(t)W$ increases from a value equal to or smaller than the predetermined threshold $\Sigma Wth$ to a value greater than the predetermined threshold $\Sigma Wth$ at a time t2 after the time t1. Therefore, the processor 21 determines through the processing in Step S106 that at or shortly after the time t2, the predetermined condition has been satisfied and the treatment target has been cut to a desired extent. At or shortly after the time t2, the control parameters Kp, Ki, and Kd are changed to the set values or second set values Kp2, Ki2, and Kd2, and the control to the heating element 18 is switched from the first phase to the second phase.

In the example of FIGS. 5 and 6, the treatment target is severed at or closely around a time t3 after the time t2. As a consequence, heat load is no longer applied from the treatment target to the heating element 18, leading to a decrease in the heat load on the heating element 18. In the example of FIGS. 5 and 6, the control to the heating element 18 is switched to the second phase, in which the temperature T(t) has lower followability to the target temperature Tx(t) than that in the first phase, at or shortly after the time t2. As the control to the heating element 18 has been switched to the second phase in which the temperature T(t) has lower followability to the target temperature Tx(t), the decrease in the heat load on the heating element 18 due to the severing leads to the beginning of a rise of the temperature T(t) from the target temperature Tx2 at or closely around the time t3. At a time t4 shortly after the time t3, the processor 21 then determines through the processing in Step S111 that the absolute value of the temperature difference Ty(t4) has become greater than the predetermined threshold Tyth. In other words, the temperature difference Ty(t4) is determined to have fallen outside the predetermined range. As a consequence, at or shortly after the time t4, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target. As a consequence, the processor 21 terminates the control that would otherwise allow the temperature T of the heating element 18 to follow the target temperature Tx.

As mentioned hereinbefore, if the treatment target has been cut to a desired extent in this embodiment, the control to the heating element 18 is switched to the second phase, in which the temperature T(t) has lower followability to the target temperature Tx(t), before the treatment target is severed. Therefore, the heat load on the heating element 18 decreases due to the severing, whereby the temperature T(t) rises from the target temperature Tx2 and the temperature difference Ty(t), a parameter representing a fluctuation in the temperature T(t) of the heating element 18 from the target temperature Tx(t), falls outside the predetermined range. Based on the falling of the temperature difference Ty(t) outside the predetermined range, the processor 21 then appropriately detects the severing of the treatment target, and reduces or terminates the output of electrical energy from the energy output source 27 to the heating element 18 so as to decrease the temperature of the heating element 18 to a temperature at which no substantial tissue degeneration occurs in the treatment target. Hence, the output of electrical energy decreases at or closely around the time of severing of the treatment target. As a consequence, it is possible to prevent the supply of electrical energy to the heating element 18 from being continued after the severing of the treatment target, whereby the treatment performance for the treatment target and the durability of the energy treatment tool are ensured.

Figure 7:
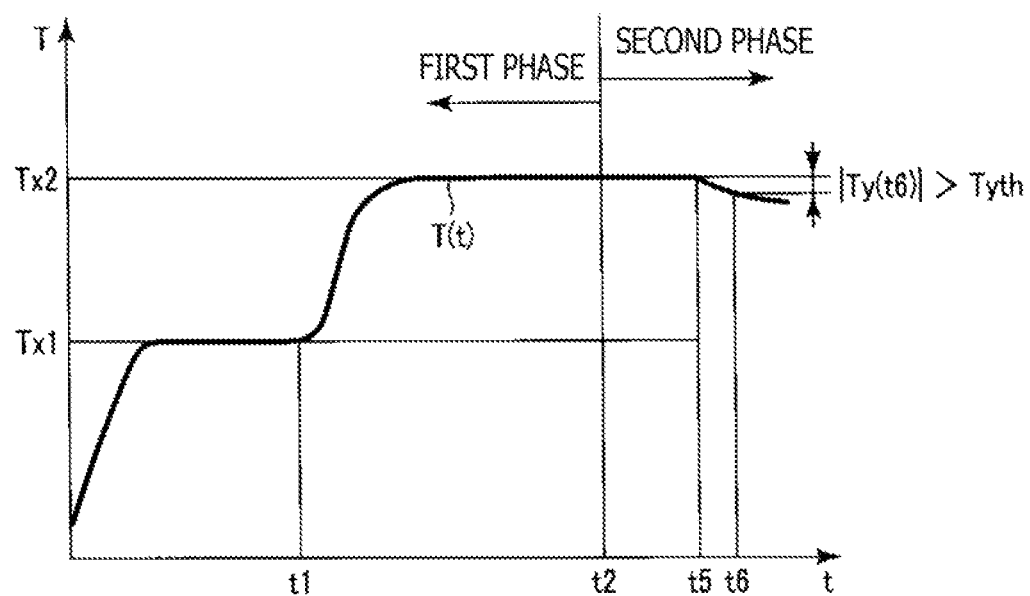
FIG. 7 is a graphic representation of another example of variations in the temperature of the heating element over time, another example being different from the example in FIG. 5, if the control is performed by the processor in the first embodiment.
Figure 8:
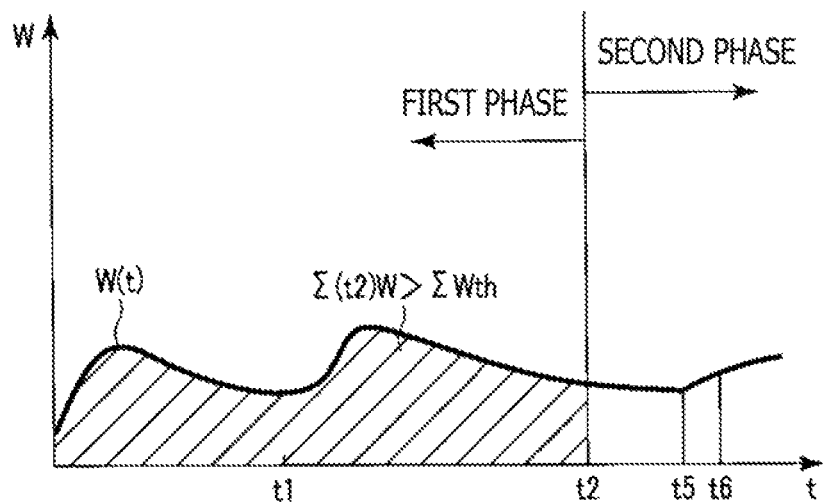
FIG. 8 is a graphic representation of variations in the output power to the heating element over time if the temperature of the heating element has varied as in FIG. 7 in the control by the processor in the first embodiment.

FIG. 7 represents an example of variations in the temperature T of the heating element 18 over time, the example being different from that in FIG. 5, if control is performed by the processor 21, and FIG. 8 represents variations in the output power W to the heating element 18 over time if the temperature T has varied as in FIG. 7. In FIGS. 7 and 8, time t is plotted along a horizontal axis. In FIG. 7, temperature T is plotted along a vertical axis, and in FIG. 8, output power W is plotted along a vertical axis. In the example represented in FIGS. 7 and 8, the temperature T(t) and output power W(t) also vary until a time t2 as in the example of FIGS. 5 and 6. At or shortly after the time t2, the control parameters Kp, Ki, and Kd are then changed from the set values or first set values Kp1, Ki1, and Kd1 to the set values or second set values Kp2, Ki2, and Kd2, and the control to the heating element 18 is switched from the first phase to the second phase.

In the example of FIGS. 7 and 8, the treatment target is severed in a state that the end effector 7 is immersed in liquid such as physiological saline. Here, the treatment target is severed at or closely around a time t5 after the time t2. Because of the severing of the treatment target with the end effector 7 located in the liquid, the end effector 7 remains at a large part thereof in contact with the cold liquid, leading to an increase in the heat load on the heating element 18. In the example of FIGS. 7 and 8, the control to the heating element 18 is switched to the second phase, in which the temperature T(t) has lower followability to the target temperature Tx(t) than that in the first phase, at or shortly after the time t2 as hereinbefore mentioned. The heat load on the heating element 18, therefore, increases due to the severing of the treatment target in the liquid, so that the temperature T(t) begins to decrease from the target temperature Tx2 at or closely around the time t5. At a time t6 shortly after the time t5, the processor 21 then determines through the processing in Step S111 that the absolute value of the temperature difference Ty(t6) has become greater than the predetermined threshold Tyth and the temperature difference Ty(t6) has fallen outside the predetermined range. As a consequence, at or shortly after the time t6, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target. As a consequence, the processor 21 terminates the control that would otherwise allow the temperature T of the heating element 18 to follow the target temperature Tx.

In this embodiment, even if the treatment target is severed with the end effector 7 immersed in the liquid, the output of electrical energy is, therefore, reduced at or closely around the time of the severing of the treatment target. As a consequence, even if the treatment target is severed in the liquid, it is possible to prevent the supply of electrical energy to the heating element 18 from being continued after the severing of the treatment target, whereby the treatment performance for the treatment target and the durability of an energy treatment tool are ensured.

Figure 9:
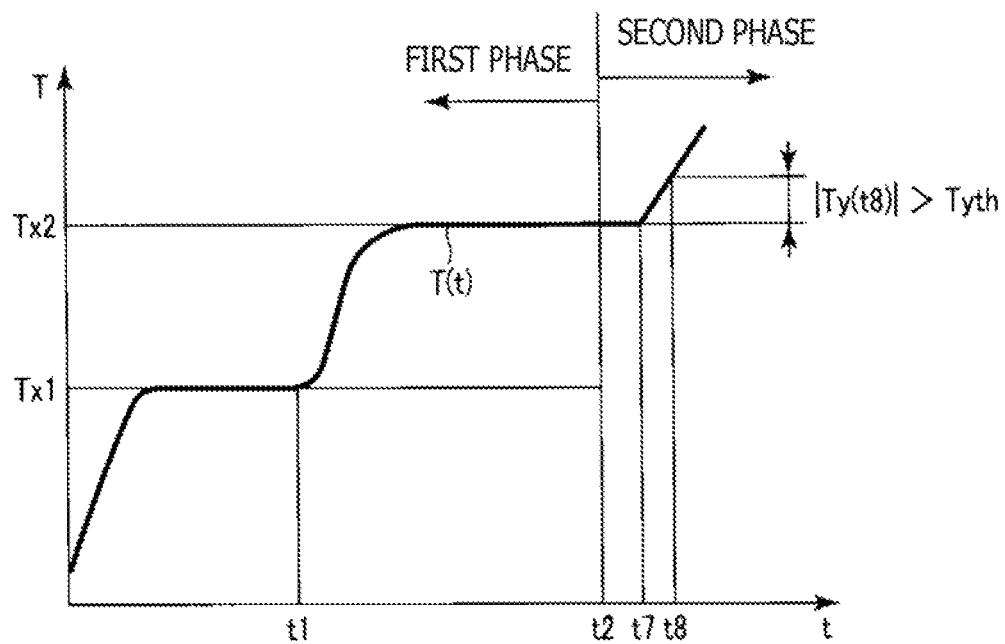
FIG. 9 is a graphic representation of a further example of variations in the temperature of the heating element over time, the further example being different from the examples in FIGS. 5 and 7, if the control is performed by the processor in the first embodiment.
Figure 10:
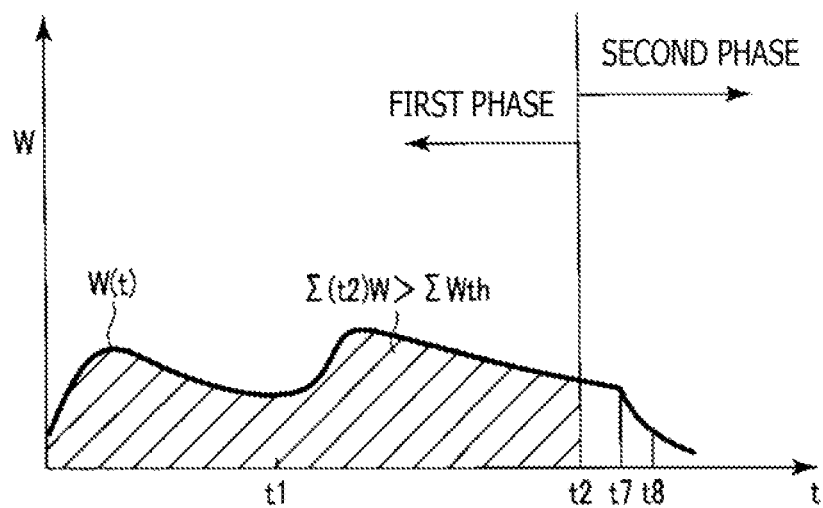
FIG. 10 is a graphic representation of variations in the output power to the heating element over time if the temperature of the heating element has varied as in FIG. 9 in the control by the processor in the first embodiment.

FIG. 9 represents a further example of variations in the temperature T of the heating element 18 over time, the further example being different from the examples in FIGS. 5 and 7, when control is performed by the processor 21, and FIG. 10 represents variations in the output power W to the heating element 18 over time when the temperature T has varied as in FIG. 9. In FIGS. 9 and 10, time t is plotted along a horizontal axis. In FIG. 9, temperature T is plotted along a vertical axis, and in FIG. 10, output power W is plotted along a vertical axis. In the example represented in FIGS. 9 and 10, the temperature T and output power W also vary until a time t2 as in the example of FIGS. 5 and 6. At or shortly after the time t2, the control parameters Kp, Ki, and Kd are then changed from the set values or first set values Kp1, Ki1, and Kd1 to the set values or second set values Kp2, Ki2, and Kd2, and the control to the heating element 18 is switched from the first phase to the second phase.

In the further example of FIGS. 9 and 10, the grasping jaws 15 and 16 open from each other at a time t7 that is after the time t2 but before the treatment target is severed. By the opening of the grasping jaws 15 and 16 from each other, one of the grasping jaws, the one grasping jaw including the heating element 18, for example, the first grasping jaw 15 is no longer in contact with the treatment target, and therefore the heat load on the heating element 18 decreases. In the further example of FIGS. 9 and 10, the control to the heating element 18 is switched to the second phase, in which the temperature T(t) has lower followability to the target temperature Tx(t) than that in the first phase, at or shortly after the time t2 as hereinbefore mentioned. The heat load on the heating element 18, therefore, decreases due to the opening operation of the end effector 7, whereby the temperature T(t) begins to rise from the target temperature Tx2 at or closely around the time t7. At a time t8 shortly after the time t7, the processor 21 then determines through the processing in Step S111 that the absolute value of the temperature difference Ty(t8) has become greater than the predetermined threshold Tyth and the temperature difference Ty(t8) has fallen outside the predetermined range. As a consequence, at or shortly after the time t8, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target. As a consequence, the processor 21 terminates the control that would otherwise allow the temperature T of the heating element 18 to follow the target temperature Tx.

In this embodiment, the output of electrical energy from the energy output source 27 to the heating element 18, therefore, decreases at or closely around the time of the opening of the grasping jaws 15 and 16 from each other before the severing of the treatment target so that the temperature of the heating element 18 decreases to a temperature at which no substantial tissue degeneration occurs in the treatment target. As a consequence, heat generated at the heating element 18 is effectively prevented from invading, for example, biological tissue other than the treatment target.

If the grasping jaws 15 and 16 have opened from each other, the increment in the temperature T(t) from the target temperature Tx(t) and the absolute value of the temperature difference Ty(t) are both large compared with those in the case where the treatment target has been severed. If the grasping jaws 15 and 16 have opened from each other, the increment in the temperature T(t) per unit time and the absolute value of the time change rate ΔTy(t) of the temperature difference Ty(t) are both large compared with those in the case where the treatment target has been severed. In a yet another example, the processor 21 determines, based on the increment in the temperature T(t) from the target temperature Tx(t), whether the falling of the temperature difference Ty(t) outside the predetermined range is due to the severing or due to the opening operation of the end effector 7. If the temperature difference Ty(t) is determined to have fallen outside the predetermined range due to the opening operation of the end effector 7, the processor 21 makes a notification by actuating, for example, a notification portion (not depicted) disposed in the control device 3. As a consequence, the surgeon can recognize whether or not the treatment target has been severed, and can also recognize whether or not the end effector 7 has opened from the state in which the treatment target is held between the grasping jaws 15 and 16. The notification portion is any one of a buzzer, a lamp, a display screen or the like.

As mentioned hereinbefore, this embodiment provides the control device 3 which can ensure the followability of the temperature T(t) of the heating element 18 to the target temperature Tx(t) until the treatment target is cut to a desired extent with heat generated at the heating element 18, and can also detect the severing of the treatment target appropriately.

Modifications

In the embodiment and the like mentioned hereinbefore, the processor 21 determines, based on, but not limited to, whether or not the integrated value Σ(t)W of the output power W is greater than the predetermined threshold ΣWth, whether or not the predetermined condition has been satisfied and whether or not the treatment target has been cut to a desired extent with heat of the heating element 18. In a modification, the processor 21 may determine, based on either the output power W(t) or the time change rate ΔW(t) of the output power W(t), whether or not the predetermined condition has been satisfied and whether or not the treatment target has been cut to a desired extent with heat of the heating element 18. If PID control is performed to allow the temperature T(t) to follow the target temperature Tx2, for example, as represented in FIGS. 5 and 6, the output power W(t) gradually increases until the temperature T(t) rises to a neighborhood of the target temperature Tx2. If the temperature T(t) has risen to the neighborhood of the target temperature Tx2, the output power W(t) then gradually decreases. In this modification, the processor 21 detects the time of switching of the output power W(t) from a gradually increasing state to a gradually decreasing state. After the output power W(t) has switched to the gradually decreasing state, the processor 21 then determines whether or not the output power W(t) is smaller than the predetermined threshold Wth. Based on the determination that the output power W(t) is smaller than the predetermined threshold Wth, the processor 21 then determines that the predetermined condition has been satisfied, and switches the control to the heating element 18 from the first phase to the second phase as in the first embodiment.

If a certain time has elapsed from the switching of the output power W(t) to the gradually decreasing state, the decrement in the output power W(t) per unit time becomes smaller as represented in FIGS. 5 and 6. Therefore, the time change rate ΔW(t) of the output power W(t), the time change rate ΔW(t) being a negative value, increases close to zero. In a further modification, after the switching of the output power W(t) to the gradually decreasing state, the processor 21 determines whether or not a predetermined time Jth has elapsed since the time of switching to the gradually decreasing state and whether or not the time change rate ΔW(t) of the output power W(t) is greater than the predetermined threshold ΔWth. Based on the determinations that the predetermined time Jth has elapsed since the time of switching to the gradually decreasing state and the time change rate ΔW(t) is greater than the predetermined threshold ΔWth, the processor 21 then determines that the predetermined condition has been satisfied, and switches the control to the heating element 18 from the first phase to the second phase as in the first embodiment.

In the PID control that allows the temperature T(t) to follow the target temperature Tx(t) and the PID control that allows the resistance value R(t) to follow the target resistance value Rx(t), respective variations over time in the output current I(t) and output voltage V(t) to the heating element 18 show similar tendency as variations over time in the output power W(t). In a yet another modification, the processor 21 may therefore determine, based on either the integrated value Σ(t)I of the output current I(t) or the integrated value Σ(t)V of the output voltage V(t) instead of the integrated value Σ(t)W of the output power W(t), whether or not the predetermined condition has been satisfied and whether or not the treatment target has been cut to a desired extent with heat of the heating element 18. In a yet further modification, the processor 21 may similarly determine, based on either the output current I(t) or the output voltage V(t), whether or not the predetermined condition has been satisfied, and in a still another modification, the processor 21 may similarly determine, based on either the time change rate 440 of the output current I(t) or the time change rate ΔV(t) of the output voltage V(t), whether or not the predetermined condition has been satisfied. In other words, based on at least one of the electrical characteristic values, i.e., the output power W, output current I and output voltage V relating to electrical energy transmitted from the energy output source 27 to the heating element 18, the integrated values of the electrical characteristic values and the time change rates of the electrical characteristic values, the processor 21 determines whether or not the predetermined condition has been satisfied and whether or not the treatment target has been cut to a desired extent with heat of the heating element 18.

In an even another modification, based on the duration Z of an output of electrical energy from the energy output source 27 to the heating element 18 from the beginning of the output, the processor 21 determines whether or not a predetermined condition has been satisfied and whether or not the treatment target has been cut to a desired extent with heat of the heating element 18. In this case, based on the fact that the duration Z is longer than a predetermined time period Zth, the processor 21 determines that the predetermined condition has been satisfied, and switches the control to the heating element 18 from the first phase to the second phase as in the first embodiment.

In the examples and the like mentioned hereinbefore, the temperature difference Ty(t) is used as a parameter that represents a fluctuation in the temperature T(t) of the heating element 18 from the target temperature Tx(t). Based on, but not limited to, falling of the temperature difference Ty(t) outside the predetermined range, the processor 21 reduces the output of electrical energy from the energy output source 27 to the heating element 18 so as to decrease the temperature of the heating element 18 to a temperature at which no substantial tissue degeneration occurs in the treatment target. In an even further modification, the time change rate ΔTy(t) of the temperature difference Ty(t) may be used as a parameter that represents a fluctuation in the temperature T(t) of the heating element 18 from the target temperature Tx(t). In this case, based on the fact that the absolute value of the time change rate ΔTy(t) of the temperature difference Ty(t) is greater than the predetermined threshold ΔTyth, in other words, the fact that the time change rate ΔTy(t) has fallen outside a predetermined range, the processor 21 reduces the output of electrical energy from the energy output source 27 to the heating element 18 so as to decrease the temperature of the heating element 18 to a temperature at which no substantial tissue degeneration occurs in the treatment target.

Figure 11:
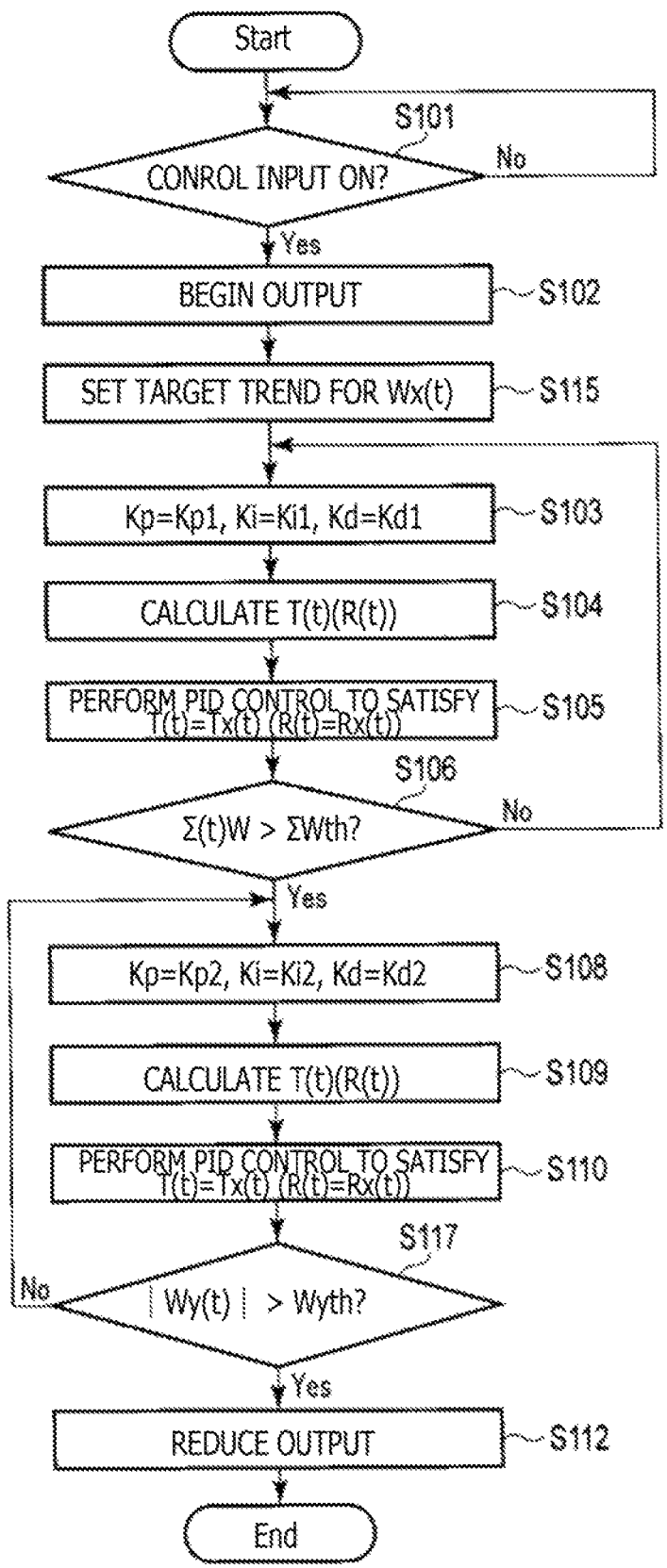
FIG. 11 is a flow chart representing processing at the processor in a modification of the first embodiment.

In the examples and the like mentioned hereinbefore, based on, but not limited to, falling of a parameter representing a fluctuation in the temperature T(t) of the heating element 18 from the target temperature Tx(t), for example, Ty(t) or ΔTy(t) outside the predetermined range, the processor 21 reduces the output of electrical energy from the energy output source 27 to the heating element 18 so as to decrease the temperature of the heating element 18 to a temperature at which no substantial tissue degeneration occurs in the treatment target, and terminates the control that would otherwise allow the temperature T of the heating element 18 to follow the target temperature Tx. In a yet still another modification represented in FIG. 11, for example, the output of electrical energy to the heating element 18 is begun in Step S102. If the target temperature Tx(t) has been set, the processor 21 sets, in Step 115, the target trend Wx(t) for the output power W(t) based on the state of an output of electrical energy to the heating element 18. Here, the target trend Wx(t) represents variations in the output power W over time if the temperature T(t) remains at the target temperature Tx(t) over time after the temperature T(t) has reached the target temperature Tx(t), in other words, if the resistance value R(t) remains at the target resistance value Rx(t) over time after the resistance value R(t) has reached the target resistance value Rx(t). Further, the target trend Wx(t) is set based on at least one of the time from the time of beginning of an output of electrical energy until the temperature T(t) reaches the target temperature Tx(t), the integrated value of the output power W(t) from the time of beginning of the output until the temperature T(t) reaches the target temperature Tx(t), and the like.

Figure 12:
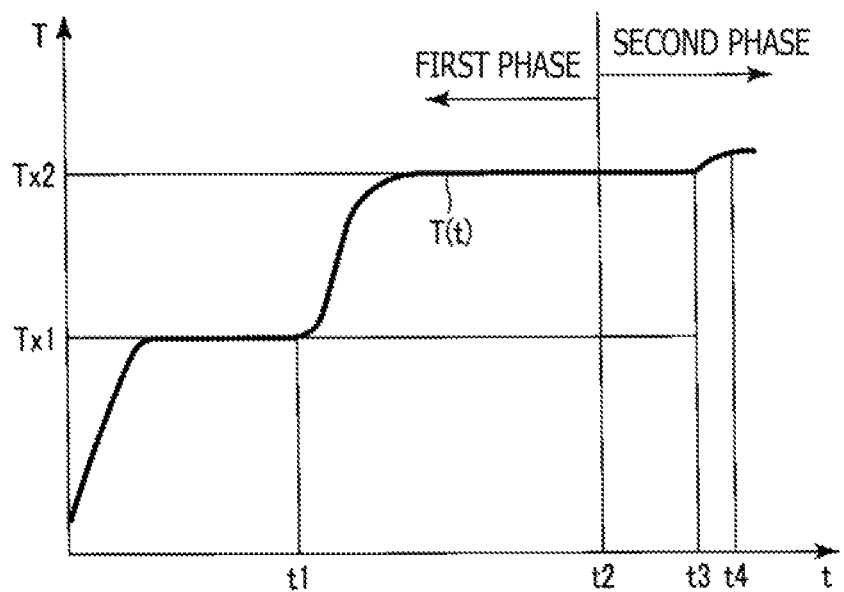
FIG. 12 is a graphic representation of an example of variations in the temperature of the heating element over time if the control is performed by the processor in the modification of the first embodiment.
Figure 13:
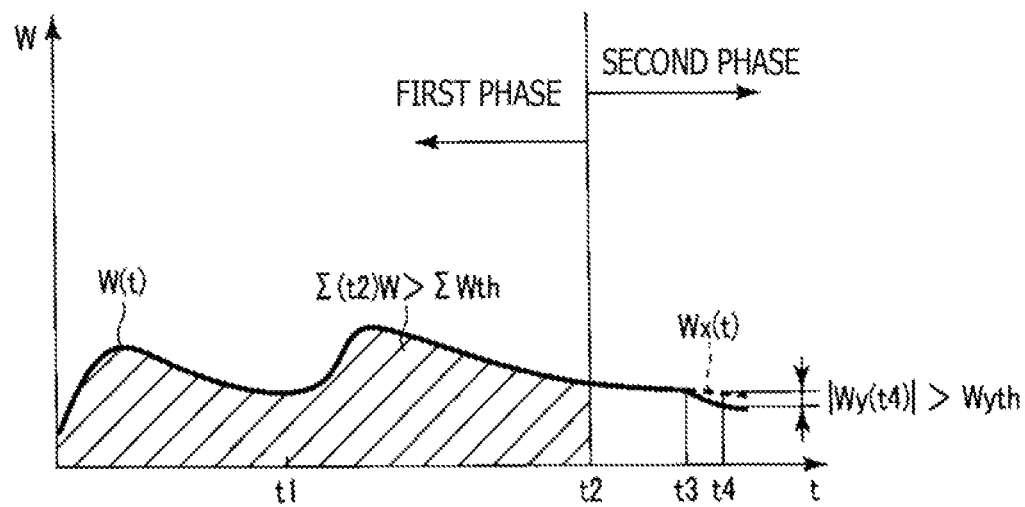
FIG. 13 is a graphic representation of variations in the output power to the heating element over time if the temperature of the heating element has varied as in FIG. 12 in the control by the processor in the modification of the first embodiment.
Figure 14:
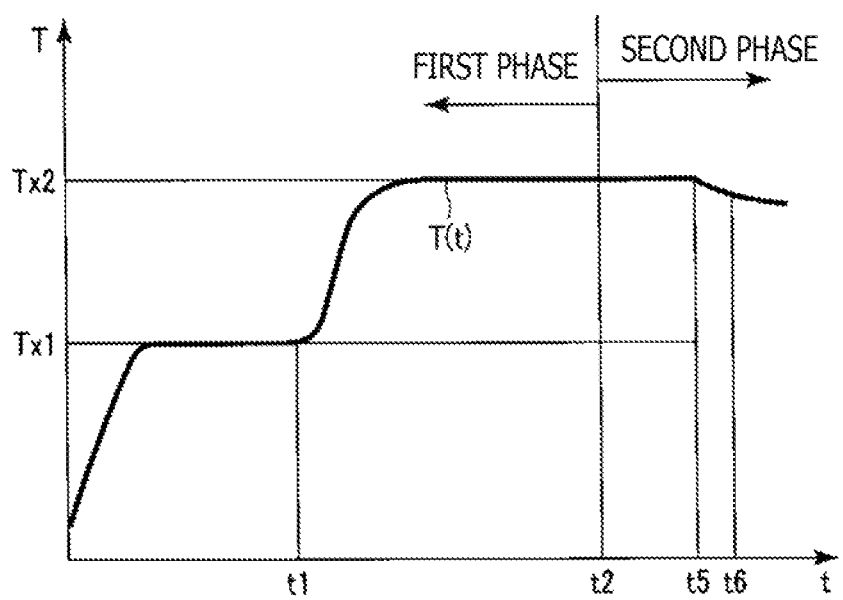
FIG. 14 is a graphic representation of another example of variations in the temperature of the heating element over time, the example being different from the example in FIG. 12, if the control is performed by the processor in the modification of the first embodiment.
Figure 15:
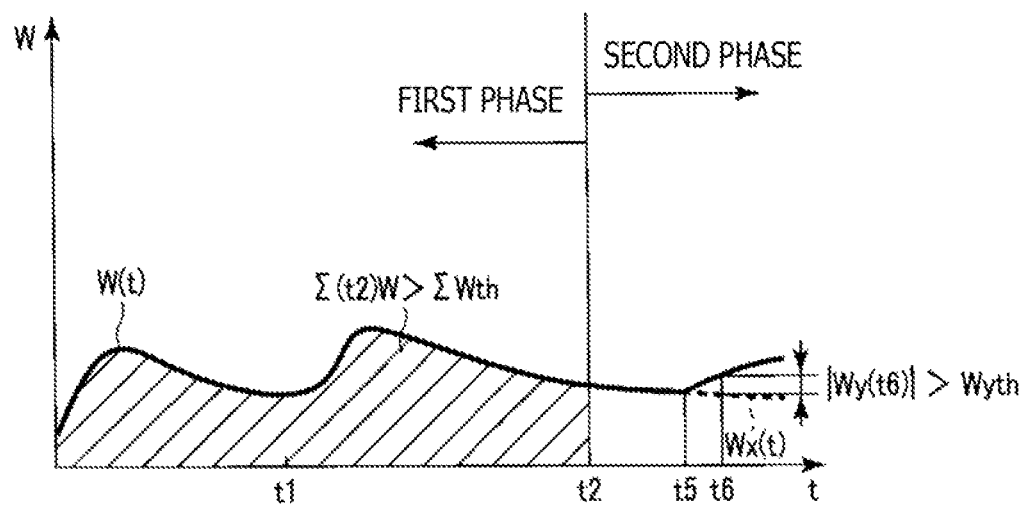
FIG. 15 is a graphic representation of variations in the output power to the heating element over time if the temperature of the heating element has varied as in FIG. 14 in the control by the processor in the modification of the first embodiment.
Figure 16:
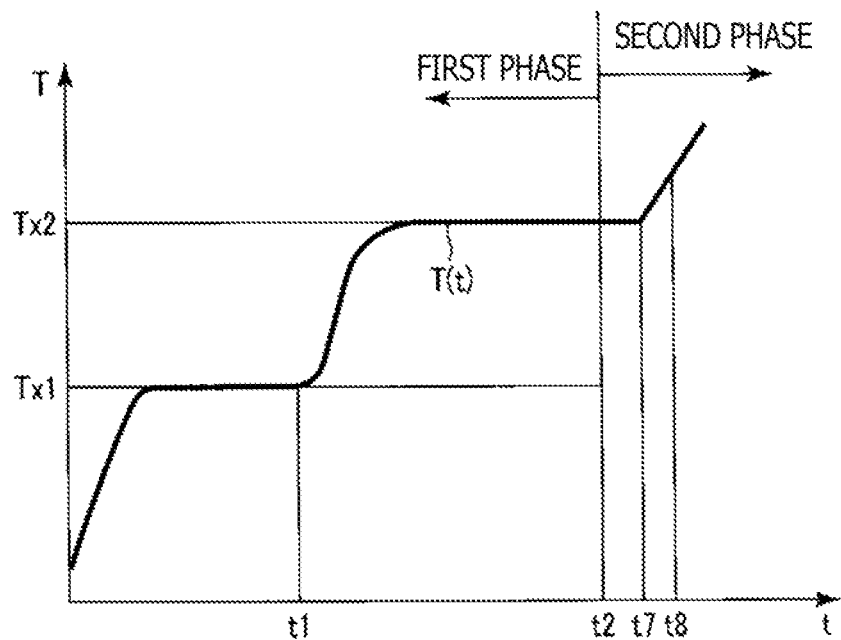
FIG. 16 is a graphic representation of a further example of variations in the temperature of the heating element over time, the further example being different from the examples in FIGS. 12 and 14, if the control is performed by the processor in the modification of the first embodiment.
Figure 17:
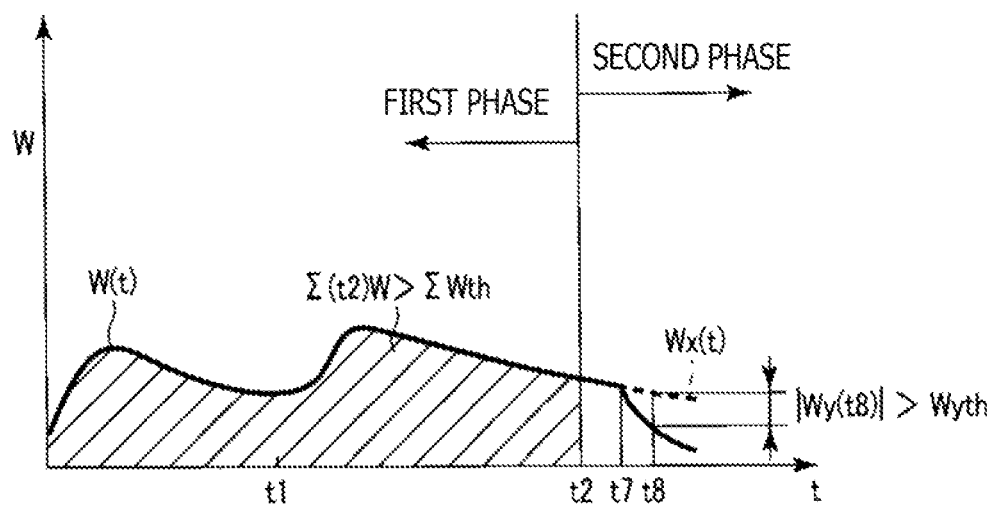
FIG. 17 is a graphic representation of variations in the output power to the heating element over time if the temperature of the heating element has varied as in FIG. 16 in the control by the processor in the modification of the first embodiment.

Now, FIG. 12 represents an example of variations in the temperature T of the heating element 18 over time if control is performed by the processor 21 in this modification, and FIG. 13 represents variations in the output power W to the heating element 18 over time if the temperature T has varied as in FIG. 12. Further, FIG. 14 represents another example of variations in the temperature T of the heating element 18 over time, another example being different from that in FIG. 12, if control is performed by the processor 21 in this modification. FIG. 15 represents variations in the output power W to the heating element 18 over time if the temperature T has varied as in FIG. 14. FIG. 16 represents a further example of variations in the temperature T of the heating element 18 over time, the further example being different from those in FIGS. 12 and 14, if control is performed by the processor 21 in this modification. FIG. 17 represents variations in the output power W to the heating element 18 over time if the temperature T has varied as in FIG. 16. In FIGS. 12 through 17, time t is plotted along a horizontal axis. In FIGS. 12, 14 and 16, temperature T is plotted along a vertical axis, and in FIGS. 13, 15 and 17, output power W is plotted along a vertical axis. In FIGS. 13, 15 and 17, target trends Wx(t) for the output power W are indicated by a dashed line.

If each target trend Wx(t) has been set, the processor 21 also performs the processing in Steps S103 to S106 in the corresponding modification as in the first embodiment. If the integrated value Σ(t)W of the output power W(t) has been determined to be greater than the predetermined threshold ΣWth in Step S106 or if Yes in Step S106, the processor 21 then determines that the predetermined condition has been satisfied, and as in the first embodiment, the processing in Steps S108 to S110 is performed. As a consequence, in this modification, the control parameters Kp, Ki, and Kd are also changed so as to lower the followability of the temperature T(t) to the target temperature Tx(t), and therefore the control to the heating element 18 is switched from the first phase to the second phase.

In this modification, however, the processing in Step S117 is performed instead of the processing in Step S111. In Step S117, a determination is made based on a power difference Wy(t) obtained by subtracting the output power W(t) from the target trend Wx(t). The power difference Wy(t) is a parameter that represents a fluctuation in the output power W(t) from the target trend Wx(t).

In this modification, if the absolute value of the power difference Wy(t) is greater than the predetermined threshold Wyth, in other words, the power difference Wy(t) has fallen outside the predetermined range in Step S117 or if Yes in Step S117, the processing proceeds to Step S112. Then, the output of electrical energy to the heating element 18 is reduced. If the absolute value of the power difference Wy(t) is equal to or smaller than the predetermined threshold Wyth, in other words, the power difference Wy(t) has fallen inside the predetermined range or if No in Step S117, on the other hand, the processing returns to Step S108. The processing in Step S108 onwards is then performed sequentially.

If the temperature T(t) and output power W(t) have varied as in the example represented in FIGS. 12 and 13, the beginning of a rise of the temperature T(t) from the target temperature Tx(t) due to the severing of the treatment target at or closely around the time t3 leads to a decrease in the output power W(t) from the target trend Wx(t). At the time t4 shortly after the time t3, the processor 21 then determines through the processing in Step S117 that the absolute value of the power difference Wy(t4) has become greater than the predetermined threshold Wyth. In other words, the power difference Wy(t4) is determined to have fallen outside the predetermined range. As a consequence, at or shortly after the time t4, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target.

If the temperature T(t) and output power W(t) have varied as in the example represented in FIGS. 14 and 15, the beginning of a decrease of the temperature T(t) from the target temperature Tx(t) due to the severing of the treatment target in the liquid at or closely around the time t5 leads to an increase in the output power W(t) from the target trend Wx(t). At the time t6 shortly after the time t5, the processor 21 then determines through the processing in Step S117 that the absolute value of the power difference Wy(t6) has become greater than the predetermined threshold Wyth and the power difference Wy(t6) has fallen outside the predetermined range. As a consequence, at or shortly after the time t6, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target.

If the temperature T(t) and output power W(t) have varied as in the example represented in FIGS. 16 and 17, the beginning of a rise of the temperature T(t) from the target temperature Tx(t) due to the opening operation of the end effector 7 at or closely around the time t7 leads to a decrease in the output power W(t) from the target trend Wx(t). At the time t8 shortly after the time t7, the processor 21 then determines through the processing in Step S117 that the absolute value of the power difference Wy(t8) has become greater than the predetermined threshold Wyth and the power difference Wy(t8) has fallen outside the predetermined range. As a consequence, at or shortly after the time t8, the processor 21 reduces, through the processing in Step S112, the output of electrical energy from the energy output source 27 to the heating element 18 so as to decrease the temperature of the heating element 18 to a temperature at which no substantial tissue degeneration occurs in the treatment target.

By performing processing as mentioned hereinbefore, these modifications also exhibit similar functions and advantageous effects as in the first embodiment.

In a yet still further modification, the time change rate $\Delta Wy(t)$ of the power difference $Wy(t)$ may be used as a parameter that represents a fluctuation in the output power $W(t)$ to the heating element 18 from the target trend $Wx(t)$. In this case, based on the fact that the absolute value of the time change rate $\Delta Wy(t)$ of the power difference $Wy(t)$ is greater than the predetermined threshold $\Delta Wyth$, in other words, the time change rate $\Delta Wy(t)$ has fallen outside the predetermined range, the processor 21 reduces the output of electrical energy from the energy output source 27 to the heating element 18 so as to decrease the temperature of the heating element 18 to a temperature at which no substantial tissue degeneration occurs in the treatment target.

In PID control that allows the temperature $T(t)$ to follow the target temperature $Tx(t)$ and PID control that allows the resistance value $R(t)$ to follow the target resistance value $Rx(t)$ as mentioned hereinbefore, respective variations over time in the output current $I(t)$ and output voltage $V(t)$ to the heating element 18 show similar tendency as variations over time in the output power $W(t)$. Therefore, in a yet even another modification, either the target trend $Ix(t)$ for the output current $I(t)$ or the target trend $Vx(t)$ for the output voltage $V(t)$ may be set instead of the target trend $Wx(t)$ for the output power $W(t)$. Here, the target trend $Ix(t)$ represents variations in the output current I over time if the temperature $T(t)$ remains at the target temperature $Tx(t)$ over time after the temperature $T(t)$ has reached the target temperature $Tx(t)$. On the other hand, the target trend $Vx(t)$ represents variations in the output voltage V over time if the temperature $T(t)$ remains at the target temperature $Tx(t)$ over time after the temperature $T(t)$ has reached the target temperature $Tx(t)$.

In a yet even further modification in which the target trend $Ix(t)$ is set, the processor 21 determines, by using a parameter that represents a fluctuation in the output current $I(t)$ from the target trend $Ix(t)$, whether or not the output of electrical energy from the energy output source 27 to the heating element 18 is reduced so as to decrease the temperature of the heating element 18 to a temperature at which no substantial tissue degeneration occurs in the treatment target. As parameters that represent a fluctuation in the output current $I(t)$ from the target trend $Ix(t)$, there are the current difference $Iy(t)$ obtained by subtracting the output current $I(t)$ from the target trend $Ix(t)$, the time change rate $\Delta Iy(t)$ of the current difference $Iy(t)$, and the like. In an example, based on the fact that the absolute value of the current difference $Iy(t)$ is greater than the predetermined threshold $Iyth$, in other words, the fact that the current difference $Iy(t)$ as the aforementioned parameter has fallen outside a predetermined range, the processor 21 reduces the output of electrical energy from the energy output source 27 to the heating element 18 so as to decrease the temperature of the heating element 18 to a temperature at which no substantial tissue degeneration occurs in the treatment target.

In an even yet further modification in which the target trend $Vx(t)$ is set, the processor 21 determines, by using a parameter that represents a fluctuation in the output current $V(t)$ from the target trend $Vx(t)$, whether or not the output of electrical energy from the energy output source 27 to the heating element 18 is reduced so as to decrease the temperature of the heating element 18 to a temperature at which no substantial tissue degeneration occurs in the treatment target. As parameters that represent a fluctuation in the output voltage $V(t)$ from the target trend $Vx(t)$, there are the voltage difference $Vy(t)$ obtained by subtracting the output voltage $V(t)$ from the target trend $Vx(t)$, the time change rate $\Delta Vy(t)$ of the voltage difference $Vy(t)$, and the like. In an example, based on the fact that the absolute value of the voltage difference $Vy(t)$ is greater than the predetermined threshold $Vyth$, in other words, the fact that the voltage difference $Vy(t)$ as the aforementioned parameter has fallen outside a predetermined range, the processor 21 reduces the output of electrical energy from the energy output source 27 to the heating element 18 so as to decrease the temperature of the heating element 18 to a temperature at which no substantial tissue degeneration occurs in the treatment target.

In some of the modifications mentioned hereinbefore, the processor 21 sets target trends for the electrical characteristic values, specifically the output power W, output current I and output voltage V relating to electrical energy to be transmitted from the energy output source 27 to the heating element 18. Based on falling of at least one parameter, which represents a fluctuation in the corresponding electrical characteristic value from the target trends, outside the predetermined range, the processor 21 reduces the output of electrical energy from the energy output source 27 to the heating element 18 so as to decrease the temperature of the heating element 18 to a temperature at which no substantial tissue degeneration occurs in the treatment target.

In still yet another modification, electrodes may be disposed on the grasping jaws 15 and 16, respectively, in addition to the heating element 18. In this case, electrical energy other than the electrical energy supplied to the heating element 18 is transmitted from the control device 3 to the electrodes. By supplying, for example, high-frequency power as electrical energy to the electrodes, a high-frequency current flows between the electrodes across the grasped treatment target. Coagulation and sealing of the treatment target are promoted by the high-frequency current.

In the embodiment mentioned hereinbefore, the end effector 7 is configured to grasp the treatment target between the paired grasping jaws 15 and 16 although the end effector 7 is not limited to such a configuration. In a still yet further modification, the end effector 7 is formed in a hook shape, a spatula shape or the like. In this case, electrical energy is also supplied from the control device 3 to the heating element 18, and heat generated at the heating element 18 is also supplied to a treatment target. Further, the temperature T of the heating element 18 is also controlled as in the embodiment and the like mentioned hereinbefore.

In the embodiment and the like mentioned hereinbefore, the processor 21 controls the heating element 18 so that the temperature $T(t)$ of the heating element 18 follows the target temperature $Tx(t)$. Based on the satisfaction of the predetermined condition, the processor 21 switches the control to the heating element 18 from the first phase to the second phase, in which the temperature $T(t)$ of the heating element 18 has lower followability to the target temperature $Tx(t)$ than that in the first phase. Based on the fact that at least one of the parameters $Ty(t)$ and $\Delta Ty(t)$ representing a fluctuation in the temperature $T(t)$ of the heating element 18 from the target temperature $Tx(t)$ has fallen outside the corresponding predetermined range or at least one of the parameters Wy(t), ΔWy(t), Iy(t), ΔIy(t), Vy(t), and ΔVy(t) representing fluctuations in the electrical characteristic values W(t), I(t), and V(t), which relate to electrical energy to be transmitted to the heating element 18, from the corresponding target trends Wx(t), Ix(t), and Vx(t) has fallen outside the corresponding predetermined range, the processor 21 then terminates the control that would otherwise allow the temperature T(t) of the heating element 18 to follow the target temperature Tx(t).

One aspect of the disclosed technology is directed to a control device for use with a treatment tool that includes a heating element to apply heat to a treatment target. The control device comprises a processor configured to set a target temperature for the heating element and to control the heating element so that temperature of the heating element follows the target temperature. The processor is configured to switch, based on satisfaction of a predetermined condition, the control of the heating element from a first phase to a second phase. A first followability of the temperature of the heating element in the first phase is higher than a second followability of the temperature in the second phase. The processor is configured to terminate the controlling of following the temperature of the heating element to the target temperature when a parameter is beyond a predetermined range wherein the parameter being defined as a fluctuation between the temperature of the heating element and the target temperature.

The control device further comprises an energy output source configured to allow the heating element to apply heat to the treatment target by transmitting electrical energy to the heating element. The processor is configured to control the temperature of the heating element so as to follow the target temperature by controlling the output of the electrical energy from the energy output source to the heating element. The processor is configured to determine based on at least one of an electrical characteristic value relating to the electrical energy to be transmitted from the energy output source to the heating element. An integrated value of the electrical characteristic value, a time change rate of the electrical characteristic value and a duration of the output of the electrical energy from beginning of the output of the electrical energy from the energy output source whether or not the predetermined condition has been satisfied. The processor is configured to calculate an integrated value of an output power from the energy output source to the heating element from beginning of the output of the electrical energy, then to determine whether or not the integrated value is greater than a predetermined threshold, and to switch the controlling of the heating element from the first phase to the second phase if the integrated value is greater than a predetermined threshold. The processor is configured to detect the time of switching from a gradually increasing state to a gradually decreasing state of an output power from the energy output source to the heating element, to determine whether or not the output power is smaller than a predetermined threshold, and to switch the control to the heating element from the first phase to the second phase if the output power is smaller than the predetermined threshold.

The processor is configured to detect the time of switching from a gradually increasing state to a gradually decreasing state of an output power from the energy output source to the heating element, to determine whether or not a predetermined time has elapsed since the time of switching to the gradually decreasing state, to determine whether or not a time change rate of the output power is greater than a predetermined threshold, and to switch the control to the heating element from the first phase to the second phase if the predetermined time has elapsed since the time of switching to the gradually decreasing state and the time change rate is greater than the predetermined threshold. The processor is configured to determine whether or not a duration of the output of the electrical energy from beginning of the output of the electrical energy from the energy output source is longer than a predetermined time period, and to switch the control of the heating element from the first phase to the second phase if the duration is longer than a predetermined time period. The processor is configured to detect a resistance value of the heating element and also to detect the temperature of the heating element based on the resistance value and a correlation between the resistance value and the temperature of the heating element. The processor is configured to reduce, based on falling of the parameter, the output of the electrical energy from the energy output source to the heating element so that the temperature of the heating element decreases to a temperature, at which no substantial tissue degeneration occurs in the treatment target, and to terminate the control that allows the temperature of the heating element to follow the target temperature. The processor is configured to control the temperature of the heating element by a feedback control, and to switch from the first phase to the second phase in controlling of the heating element by changing a control parameter of the feedback control from a first set value to a second set value.

Another aspect of the disclosed technology is directed to a control device for use with a treatment tool that includes a heating element. The control device comprises an energy output source configured to transmit electrical energy to the heating element so as to apply heat to a treatment target. A processor is configured to be in electrical communication with the energy output source so as to control temperature of the heating element by controlling the output of the electrical energy from the energy output source. The processor is configured to set a target temperature for the heating element and to control the output of the electrical energy so that the temperature of the heating element follows the target temperature. Based on an output state of the electrical energy from the energy output source to the heating element, to set a target trend for an electrical characteristic value relating to the electrical energy, the target trend representing variations in the electrical characteristic value over time if the temperature of the heating element is maintained at the target temperature over time after the temperature of the heating element has reached the target temperature. Based on satisfaction of a predetermined condition, to switch the control of the electrical energy, which is to be transmitted to the heating element from a first phase to a second phase wherein a first followability of the temperature of the heating element in the first phase is higher than a second followability of the temperature in the second phase, and to reduce the output of the electrical energy from the energy output source to the heating element so that the temperature of the heating element decreases to a temperature, at which no substantial tissue degeneration occurs in the treatment target, when a parameter is beyond a predetermined range wherein the parameter being defined as a fluctuation between the electrical characteristic value and the target trend. The processor uses, as the electrical characteristic value, one of output power, output current and output voltage from the energy output source to the heating element.

A Further aspect of the disclosed technology is directed to a treatment system comprises an energy treatment tool. A control device is configured to be attached to the energy treatment tool so as to enable the treatment system to conduct a treatment on a body tissue. The control device comprises an energy output source configured to transmit electrical energy to a heating element so as to apply heat to a treatment target. A processor is configured to be in electrical communication with the energy output source so as to control temperature of the heating element by controlling the output of the electrical energy from the energy output source. The processor is configured by setting a target temperature for the heating element and controlling the output of the electrical energy so that the temperature of the heating element follows the target temperature. Next, setting a target trend for an electrical characteristic value relating to the electrical energy, the target trend representing variations in the electrical characteristic value over time if the temperature of the heating element is maintained at the target temperature over time after the temperature of the heating element has reached the target temperature. Next, switching the control of the electrical energy, which is to be transmitted to the heating element from a first phase to a second phase wherein a first followability of the temperature of the heating element in the first phase is higher than a second followability of the temperature in the second phase. Finally, reducing the output of the electrical energy from the energy output source to the heating element so that the temperature of the heating element decreases to a temperature, at which no substantial tissue degeneration occurs in the treatment target, when a parameter is beyond a predetermined range wherein the parameter being defined as a fluctuation between the electrical characteristic value and the target trend.

The processor is configured to calculate an integrated value of an output power from the energy output source to the heating element from beginning of the output of the electrical energy. Then, to determine whether or not the integrated value is greater than a predetermined threshold, and to switch the controlling of the heating element from the first phase to the second phase if the integrated value is greater than a predetermined threshold. The processor is configured to detect the time of switching from a gradually increasing state to a gradually decreasing state of an output power from the energy output source to the heating element, to determine whether or not the output power is smaller than a predetermined threshold and to switch the control to the heating element from the first phase to the second phase if the output power is smaller than the predetermined threshold. The processor is configured to detect the time of switching from a gradually increasing state to a gradually decreasing state of an output power from the energy output source to the heating element, to determine whether or not the output power is smaller than a predetermined threshold, and to switch the control to the heating element from the first phase to the second phase if the output power is smaller than the predetermined threshold.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future. The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:
1. A control device for use with a treatment tool that includes a heating element to apply heat, to a treatment target, the control device comprising:
   a processor configured to:
      set a target temperature for the heating element;
      control the heating element so that temperature of the heating element follows the set target temperature by controlling an output of electrical energy from an energy output source to the heating element, the energy output source being configured to allow the heating element to apply heat to the treatment target by transmitting the electrical energy to the heating element;
      obtain a first parameter relating to the output of the electrical energy from the energy output source to the heating element;

determine whether the first parameter relating to the output of the electrical energy from the energy output source to the heating element satisfies a predetermined condition;

in response to satisfying the predetermined condition, switch the control of the heating element from a first phase to a second phase such that a first followability of the temperature of the heating element in the first phase is higher than a second followability of the temperature in the second phase; and terminate the controlling of following the temperature of the heating element to the set target temperature when a second parameter defined by a fluctuation between the temperature of the heating element and the target temperature exceeds a predetermined range.

2. The control device of claim 1, further comprising the energy output source.

3. The control device of claim 2, wherein, based on at least one of an electrical characteristic value relating to the electrical energy to be transmitted from the energy output source to the heating element, the processor is configured to determine:

an integrated value of the electrical characteristic value, a time change rate of the electrical characteristic value, and a duration of the output of the electrical energy from beginning of the output of the electrical energy from the energy output source whether the first parameter satisfies the predetermined condition.

4. The control device of claim 2, wherein the processor is configured to:

calculate an integrated value of an output power from the energy output source to the heating element from beginning of the output of the electrical energy as the first parameter, determine whether the integrated value is greater than a predetermined threshold, and switch the controlling of the heating element from the first phase to the second phase when the integrated value is greater than a predetermined threshold.

5. The control device of claim 2, wherein the processor is configured to:

detect a time of switching from an increasing state to a decreasing state of an output power from the energy output source to the heating element, determine whether the output power, which is the first parameter, is smaller than a predetermined threshold, and switch the control to the heating element from the first phase to the second phase when the output power is smaller than the predetermined threshold.

6. The control device of claim 2, wherein the processor is configured to:

detect a time of switching from an increasing state to a decreasing state of an output power from the energy output source to the heating element, calculate, as one of two first parameters, an elapsed time since the time of switching to the decreasing state and determine whether the elapsed time since the time of switching to the decreasing state is longer than a predetermined time period, determine whether a time change rate of the output power, which is another one of the two first parameters, is greater than a predetermined threshold, and switch the control to the heating element from the first phase to the second phase when the elapsed time since the time of switching to the decreasing state is longer than the predetermined time period and the time change rate is greater than the predetermined threshold.

7. The control device of claim 2, wherein the processor is configured to:

determine whether a duration of the output of the electrical energy, which is the first parameter, from a beginning of the output of the electrical energy from the energy output source is longer than a predetermined time period, and switch the control to the heating element from the first phase to the second phase when the duration is longer than the predetermined time period.

8. The control device of claim 2, wherein the processor is configured to detect a resistance value of the heating element and detect the temperature of the heating element based on the resistance value and a correlation between the resistance value and the temperature of the heating element.

9. The control device of claim 2, wherein the processor is configured to:

reduce, based on falling of the second parameter, the output of the electrical energy from the energy output source to the heating element so that the temperature of the heating element decreases to a temperature, at which no substantial tissue degeneration occurs in the treatment target, and terminate the control that allows the temperature of the heating element to follow the target temperature.

10. The control device of claim 1, wherein the processor is configured to:

control the temperature of the heating element by a feedback control, and switch from the first phase to the second phase in controlling of the heating element by changing a control parameter of the feedback control from a first set value to a second set value.

11. A control device for use with a treatment tool that includes a heating element, the control device comprising:

an energy output source configured to transmit electrical energy to the heating element so as to apply heat to a treatment target; and a processor configured to be in electrical communication with the energy output source so as to control temperature of the heating element by controlling an output of the electrical energy from the energy output source, the processor being configured to:

set a target temperature for the heating element, control the output of the electrical energy so that the temperature of the heating element follows the target temperature based on an output state of the electrical energy from the energy output source to the heating element, set a target trend of an electrical characteristic value relating to the electrical energy, the target trend representing variations in the electrical characteristic value over time when the temperature of the heating element is maintained at the target temperature over time after the temperature of the heating element has reached the target temperature, based on satisfaction of a predetermined condition, switch the control of the electrical energy, which is to be transmitted to the heating element from a first phase to a second phase, such that a first followability of the temperature of the heating element in the first phase is higher than a second followability of the temperature in the second phase, and reduce the output of the electrical energy from the energy output source to the heating element so that the temperature of the heating element decreases to a temperature, at which no substantial tissue degeneration occurs in the treatment target, when a parameter is beyond a predetermined range wherein the parameter being defined as a fluctuation between the electrical characteristic value and the target trend.

12. The control device of claim 11, wherein the processor is configured to set, as the electrical characteristic value, one of output power, output current, and output voltage from the energy output source to the heating element.

13. A treatment system comprising:
an energy treatment tool; and
a control device configured to be attached to the energy treatment tool so as to enable the treatment system to conduct a treatment on a body tissue, the control device including an energy output source configured to transmit electrical energy to a heating element so as to apply heat to a treatment target, and a processor configured to be in electrical communication with the energy output source so as to control temperature of the heating element by controlling the output of the electrical energy from the energy output source, the processor being configured to perform:
setting a target temperature for the heating element,
controlling the output of the electrical energy so that the temperature of the heating element follows the set target temperature by controlling the output of the electrical energy from the energy output source to the heating element,
setting a target trend of an electrical characteristic value relating to the electrical energy, the target trend representing variations in the electrical characteristic value over time when the temperature of the heating element is maintained at the target temperature over time after the temperature of the heating element has reached the target temperature,
obtaining a first parameter relating to the output of the electrical energy from the energy output source to the heating element,
determining whether the first parameter relating to the output of the electrical energy from the energy output source to the heating element satisfies a predetermined condition,
switching the control of the electrical energy, when the first parameter satisfies the predetermined condition, from a first phase to a second phase such that a first followability of the temperature of the heating element in the first phase is higher than a second followability of the temperature in the second phase, and
reducing the output of the electrical energy from the energy output source to the heating element so that the temperature of the heating element decreases to a temperature, at which no substantial tissue degeneration occurs in the treatment target, when a second parameter is beyond a predetermined range, the second parameter being defined as a fluctuation between the electrical characteristic value and the target trend.

14. The treatment system of claim 13, wherein the processor is configured to:
calculate an integrated value of an output power from the energy output source to the heating element from a beginning of the output of the electrical energy as the first parameter,
determine whether the integrated value is greater than a predetermined threshold, and
switch the controlling of the heating element from the first phase to the second phase when the integrated value is greater than a predetermined threshold.

15. The treatment system of claim 13, wherein the processor is configured to:
detect a time of switching from an increasing state to a decreasing state of an output power from the energy output source to the heating element,
determine whether the output power, which is the first parameter, is smaller than a predetermined threshold, and
switch the control to the heating element from the first phase to the second phase when the output power is smaller than the predetermined threshold.

* * * * *